US010758167B2

(12) United States Patent
Millerd

(10) Patent No.: US 10,758,167 B2
(45) Date of Patent: *Sep. 1, 2020

(54) PASSIVE SAFETY I.V. BLOOD COLLECTION CATHETER

(71) Applicant: MMI, LLC, San Diego, CA (US)

(72) Inventor: Donald L. Millerd, San Diego, CA (US)

(73) Assignee: MMI, LLC, San Diego, CA (US)

( * ) Notice: Subject to any disclaimer, the term of this patent is extended or adjusted under 35 U.S.C. 154(b) by 297 days.

This patent is subject to a terminal disclaimer.

(21) Appl. No.: 15/280,040

(22) Filed: Sep. 29, 2016

(65) Prior Publication Data
US 2017/0014061 A1    Jan. 19, 2017

Related U.S. Application Data

(63) Continuation of application No. 14/068,630, filed on Oct. 31, 2013, now Pat. No. 9,456,775.
(Continued)

(51) Int. Cl.
*A61B 5/15* (2006.01)
*A61M 5/178* (2006.01)
(Continued)

(52) U.S. Cl.
CPC ...... *A61B 5/150389* (2013.01); *A61B 5/1444* (2013.01); *A61B 5/15003* (2013.01);
(Continued)

(58) Field of Classification Search
CPC .. A61M 25/0631; A61M 5/326; A61B 5/1444
See application file for complete search history.

(56) References Cited

U.S. PATENT DOCUMENTS 5,053,014 A    10/1991  Van Heugten
5,125,414 A     6/1992  Dysarz
(Continued)

FOREIGN PATENT DOCUMENTS

AU    2012201851    4/2012
AU    2011336340    6/2012
(Continued)

OTHER PUBLICATIONS

Serial No. PCT/US2010/036922, WIPO, IPRP dated Jan. 4, 2012, 9 pages.
(Continued)

*Primary Examiner* — Patrick Fernandes
(74) *Attorney, Agent, or Firm* — John V. Daniluck; Dentons Bingham Greenebaum LLP

(57) ABSTRACT

Apparatus and methods for a single, handheld device that provides for both insertion of a catheter and collection of a fluid. Some embodiments further include a needle that assists in the insertion of the catheter into a blood vessel, and which includes a retraction feature that protects the user from an accidental needle stick when the device is ready for disposal. Still further embodiments include a protective cover that prevents a user from accidentally being stuck by a second needle used for the introduction of the patient's blood into a collection device.

20 Claims, 26 Drawing Sheets

Related U.S. Application Data

(60) Provisional application No. 61/874,771, filed on Sep. 6, 2013.

(51) Int. Cl.
*A61B 5/154* (2006.01)
*A61M 25/00* (2006.01)
*A61M 5/32* (2006.01)
*A61M 25/06* (2006.01)

(52) U.S. Cl.
CPC ........ *A61B 5/154* (2013.01); *A61B 5/150213* (2013.01); *A61B 5/150221* (2013.01); *A61B 5/150503* (2013.01); *A61B 5/150572* (2013.01); *A61B 5/150656* (2013.01); *A61B 5/150732* (2013.01); *A61M 5/178* (2013.01); *A61M 5/3202* (2013.01); *A61M 5/322* (2013.01); *A61M 5/3213* (2013.01); *A61M 5/3232* (2013.01); *A61M 25/00* (2013.01); *A61M 25/0606* (2013.01); *A61M 25/0631* (2013.01)

(56) References Cited

U.S. PATENT DOCUMENTS

| | | | |
|---|---|---|---|
| 5,188,599 A | 2/1993 | Botich et al. | |
| 5,205,829 A | 4/1993 | Lituchy | |
| 5,403,283 A | 4/1995 | Luther | |
| 5,501,675 A | 3/1996 | Erskine | |
| 5,616,135 A | 4/1997 | Thorne et al. | |
| 5,755,709 A | 5/1998 | Cuppy | |
| 5,800,395 A | 9/1998 | Botich et al. | |
| 5,989,220 A | 11/1999 | Shaw et al. | |
| 6,004,278 A | 12/1999 | Botich | |
| 6,436,070 B1 | 8/2002 | Botich et al. | |
| 6,607,511 B2 | 8/2003 | Haleth et al. | |
| 6,616,637 B2 | 9/2003 | Alexander et al. | |
| 6,726,658 B2 | 4/2004 | Hochman | |
| 6,832,992 B2 | 12/2004 | Wilkinson | |
| 6,855,130 B2 | 2/2005 | Saulenas et al. | |
| 6,974,423 B2 | 12/2005 | Zurcher | |
| 7,101,351 B2 | 9/2006 | Crawford et al. | |
| 7,118,538 B2 | 10/2006 | Konrad | |
| 7,357,783 B2 | 4/2008 | Millerd | |
| 7,753,887 B2 | 7/2010 | Botich et al. | |
| 7,766,879 B2 | 8/2010 | Tan et al. | |
| 7,985,216 B2 | 7/2011 | Dailey et al. | |
| 8,052,653 B2 | 11/2011 | Gratwohl et al. | |
| 8,062,252 B2 | 11/2011 | Alheidt et al. | |
| 8,062,265 B2 | 11/2011 | Millerd | |
| 8,167,820 B2 | 5/2012 | Mahurkar | |
| 8,216,187 B2 | 7/2012 | Millerd et al. | |
| 8,216,188 B2 | 7/2012 | Millerd et al. | |
| 8,282,605 B2 | 10/2012 | Tan et al. | |
| 8,303,543 B2 | 11/2012 | Abulhaj | |
| 8,333,738 B2 | 12/2012 | Millerd | |
| 8,465,441 B2 | 6/2013 | Srivastsa et al. | |
| 8,469,927 B2 | 6/2013 | Shaw et al. | |
| 8,486,024 B2 | 7/2013 | Steube | |
| 8,512,295 B2 | 8/2013 | Evans et al. | |
| 10,085,680 B2 | 10/2018 | Crawford et al. | |
| 2002/0103461 A1 | 8/2002 | Asbaghi | |
| 2003/0078540 A1 | 4/2003 | Saulenas | |
| 2003/0171695 A1* | 9/2003 | Zurcher | A61M 5/3232 600/577 |
| 2003/0199827 A1 | 10/2003 | Thorne | |
| 2004/0087875 A1 | 5/2004 | Asbaghi | |
| 2004/0092872 A1 | 5/2004 | Botich | |
| 2004/0122373 A1 | 6/2004 | Botich et al. | |
| 2004/0127854 A1 | 7/2004 | Leinsing | |
| 2004/0147855 A1 | 7/2004 | Marsden | |
| 2004/0249309 A1 | 12/2004 | Yang | |
| 2005/0245875 A1 | 11/2005 | Restelli et al. | |
| 2005/0267384 A1 | 12/2005 | Sauer et al. | |
| 2006/0155244 A1* | 7/2006 | Popov | A61M 25/0625 604/162 |
| 2007/0088278 A1 | 4/2007 | Shue | |
| 2007/0088279 A1 | 4/2007 | Shue et al. | |
| 2010/0168614 A1 | 7/2010 | Crawford | |
| 2010/0210934 A1 | 8/2010 | Belson | |
| 2010/0241029 A1 | 9/2010 | Mahurkar | |
| 2010/0317999 A1 | 12/2010 | Shaw et al. | |
| 2010/0331781 A1 | 12/2010 | Millerd et al. | |
| 2010/0331787 A1 | 12/2010 | Glenn | |
| 2011/0166474 A1 | 7/2011 | Crawford et al. | |
| 2011/0166475 A1 | 7/2011 | Crawford et al. | |
| 2011/0166476 A1 | 7/2011 | Crawford et al. | |
| 2012/0004574 A1 | 1/2012 | Srivatsa et al. | |
| 2012/0016307 A1 | 1/2012 | Burkholz et al. | |
| 2012/0220956 A1 | 8/2012 | Kuracina et al. | |
| 2012/0259243 A1 | 11/2012 | Shaw et al. | |
| 2014/0171830 A1 | 6/2014 | Shaw et al. | |
| 2015/0073303 A1 | 3/2015 | Shaw et al. | |

FOREIGN PATENT DOCUMENTS

| | | |
|---|---|---|
| CA | 2228264 | 12/1997 |
| CA | 2456597 | 2/2003 |
| CA | 2406994 | 9/2010 |
| CN | 101674772 | 3/2010 |
| EP | 0002028 | 5/1979 |
| EP | 1884257 | 2/2008 |
| EP | 2145640 | 1/2010 |
| EP | 1430834 | 2/2013 |
| JP | 2009136397 | 6/2009 |
| JP | 4754147 | 8/2011 |
| WO | 9309824 | 5/1993 |
| WO | 9824493 | 6/1998 |
| WO | 2008109845 | 9/2008 |
| WO | 2008137956 | 11/2008 |
| WO | 2011002568 | 1/2011 |
| WO | 2011066022 | 6/2011 |
| WO | 2011100039 | 8/2011 |
| WO | 2012003343 | 1/2012 |
| WO | 2012015644 | 2/2012 |
| WO | 2012030663 | 3/2012 |
| WO | 2012067778 | 5/2012 |
| WO | 2012075402 | 6/2012 |
| WO | 2012118718 | 9/2012 |
| WO | 2012162821 | 12/2012 |
| WO | 2012174109 | 12/2012 |
| WO | 2013126819 | 8/2013 |
| WO | 2015067106 | 5/2015 |

OTHER PUBLICATIONS

Serial No. PCT/US2010/036922, ISR/Written Opinion dated Jul. 27, 2010, 10 pages.
Serial No. PCT/US11/49428, ISR/Written Opinion dated Dec. 22, 2011, 8 pages.
KIPO, Serial No. PCT/US2014/052515, Search Report and Written Opinion, 15 pages dated Nov. 24, 2014.
APO, Serial No. AU 2014315524, Examination Report, 5 pp. dated Aug. 8, 2018.
SIPO, Serial No. CN 201480056922.2, First Office Action, dated Apr. 19, 2018, 5 pp. Apr. 19, 2018.
Response Filed, Serial No. CN 201480056922.2, Aug. 31, 2018, 24 pgs. Aug. 31, 2018.
EPO, Serial No. EP 14841730.6, Search Report, dated Mar. 13, 2017, 9 pp. Mar. 13, 2017.
Response to Search Report filed, Serial No. EP 14841730.6, dated Oct. 9, 2017, 4pp. Oct. 9, 2017.
EPO, Serial No. EP 18177109.8, Search Report, dated Aug. 14, 2018, 8 pp. Aug. 14, 2018.
AU 2014315524, Response to Examiners Report, 41 pgs dated May 13, 2019.
SIPO, Serial No. CN 201480056922.2, 2nd Office Action, 12 pages dated Dec. 14, 2018.
CN 201480056922.2, Response to 2nd Office Action, 10 pgs dated Apr. 19, 2019.

(56) References Cited

OTHER PUBLICATIONS

EP 18177109.8, Response to Search Report, 14 pgs dated May 7, 2019.
SIPO, Serial No. 201480056922.2, 3rd Office Action, 11 pgs dated Jun. 11, 2019.
Response filed, Serial No. CN 201480056922.2, 15 pgs dated Jun. 11, 2019.
EPO, Serial No. 19216099.2, Examination Report, 8 pgs dated Mar. 2, 2020.

* cited by examiner

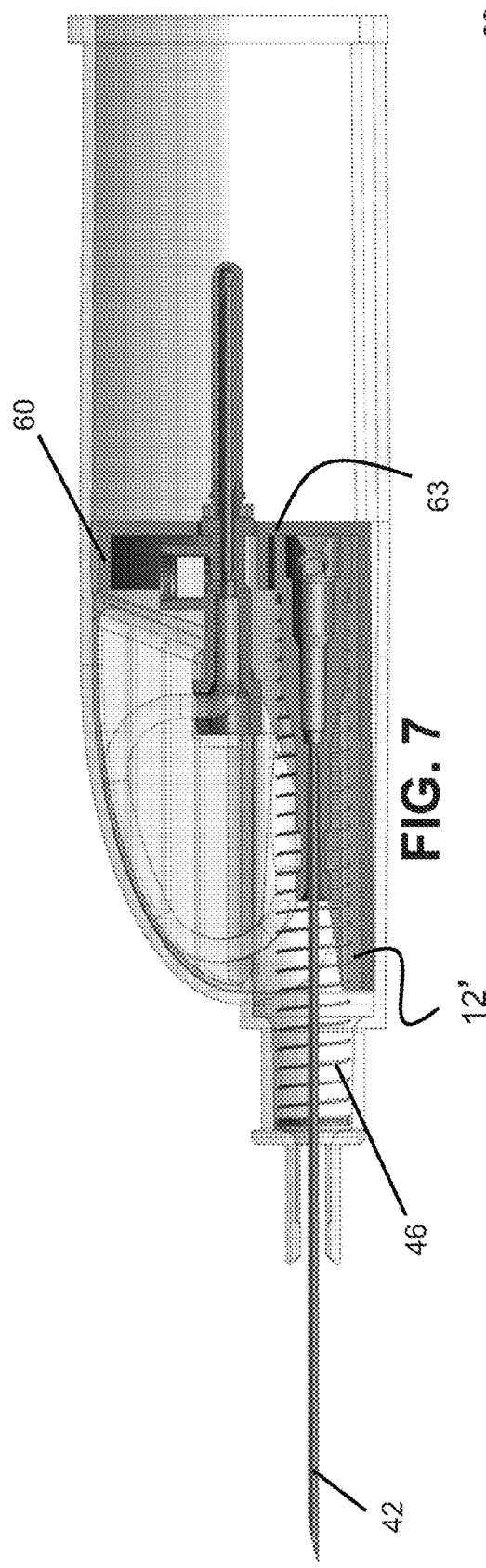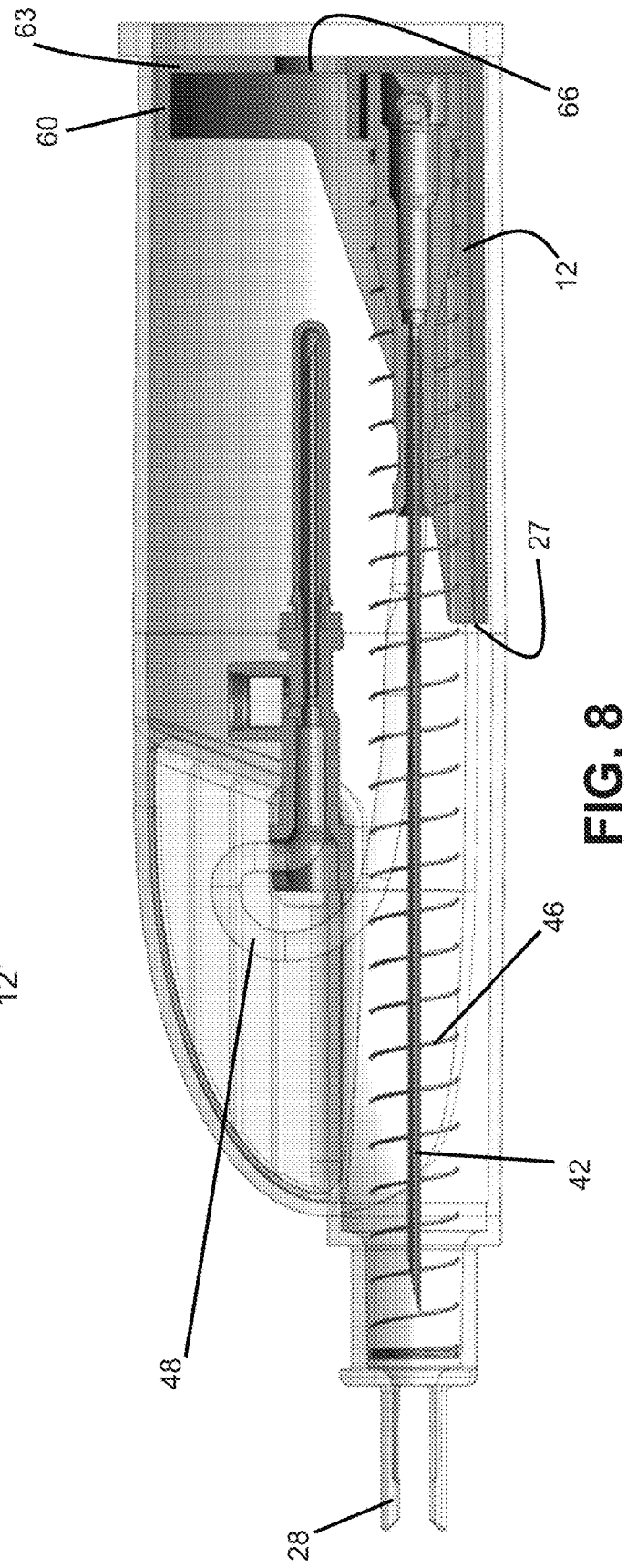

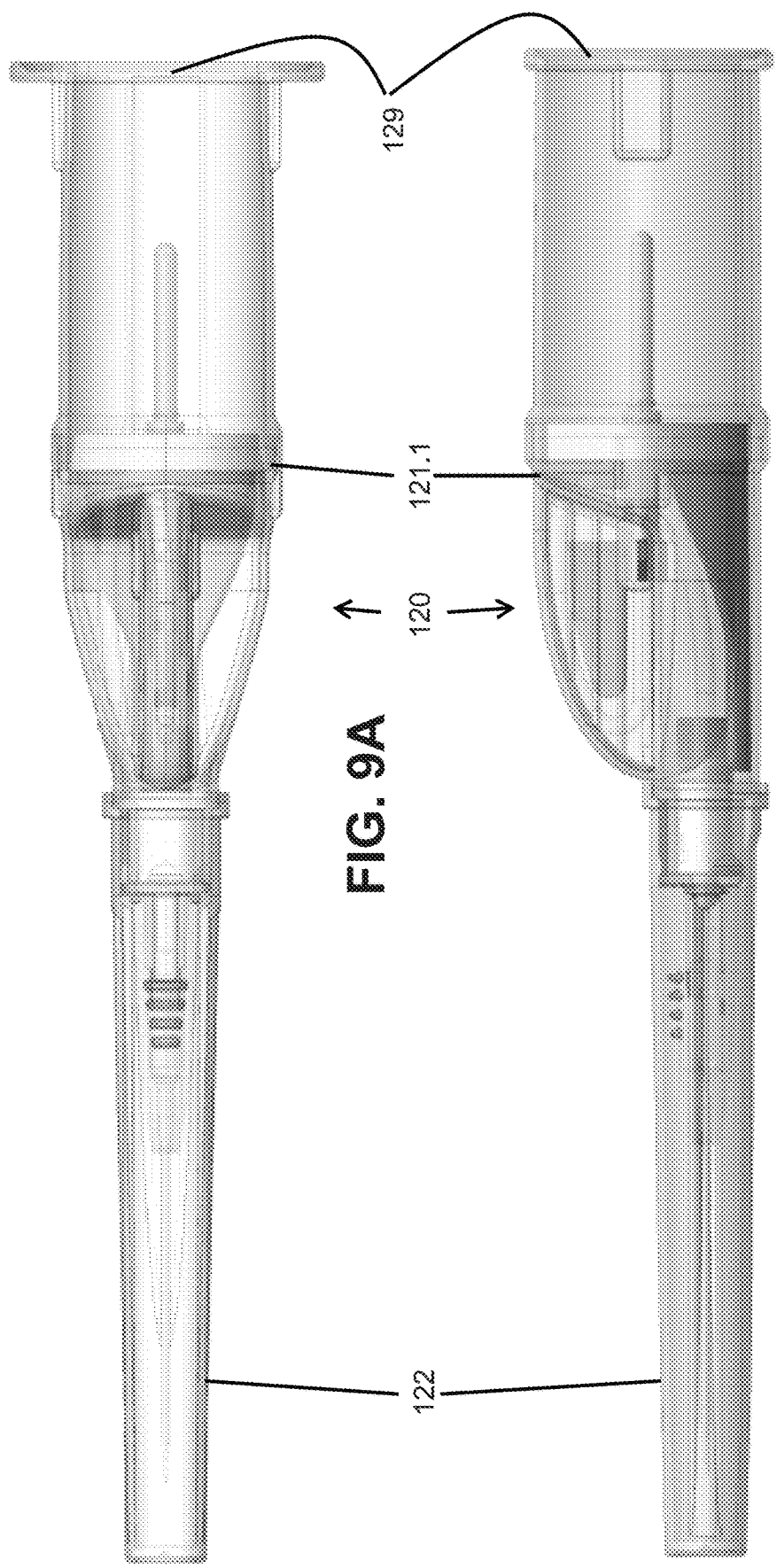

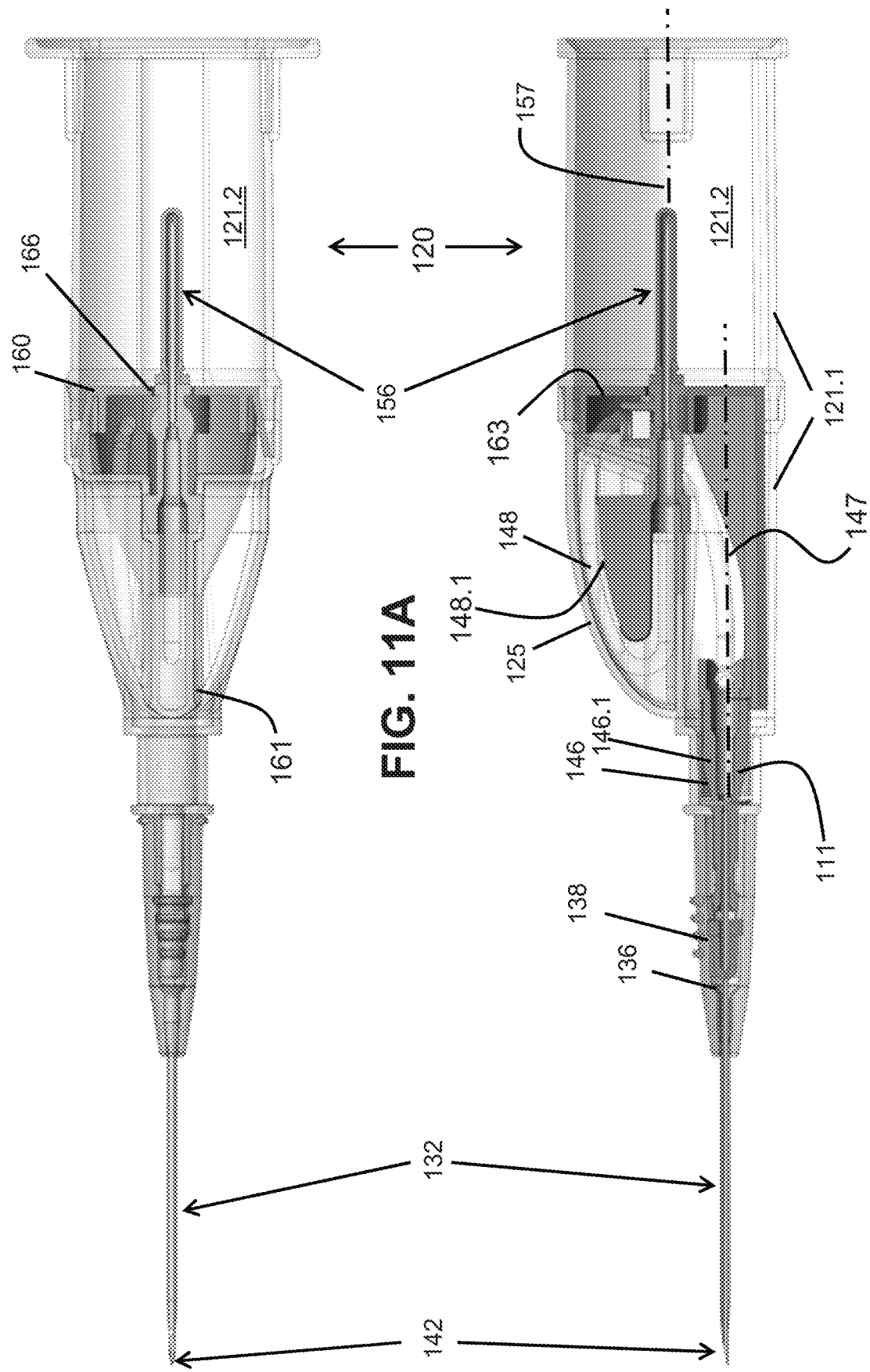

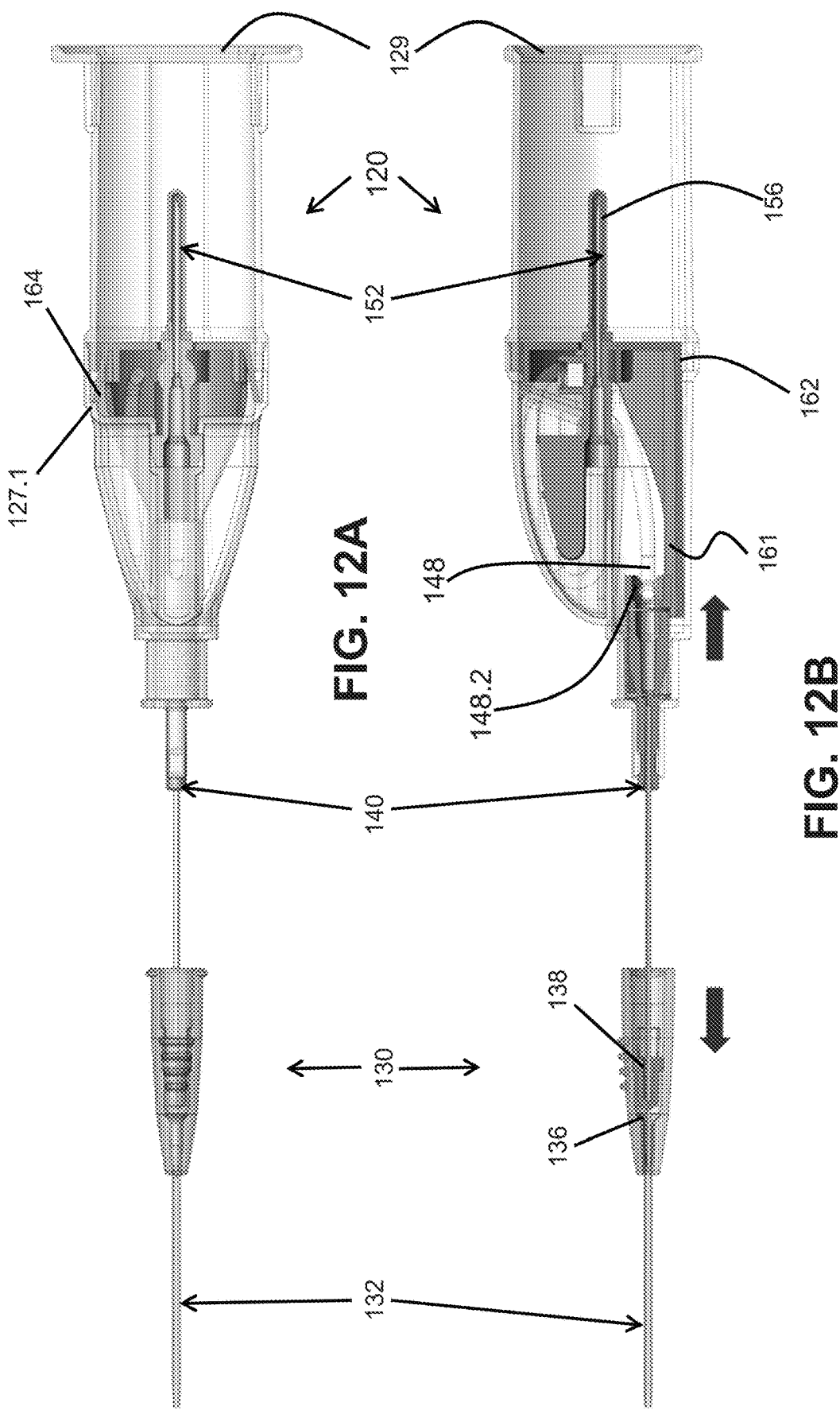

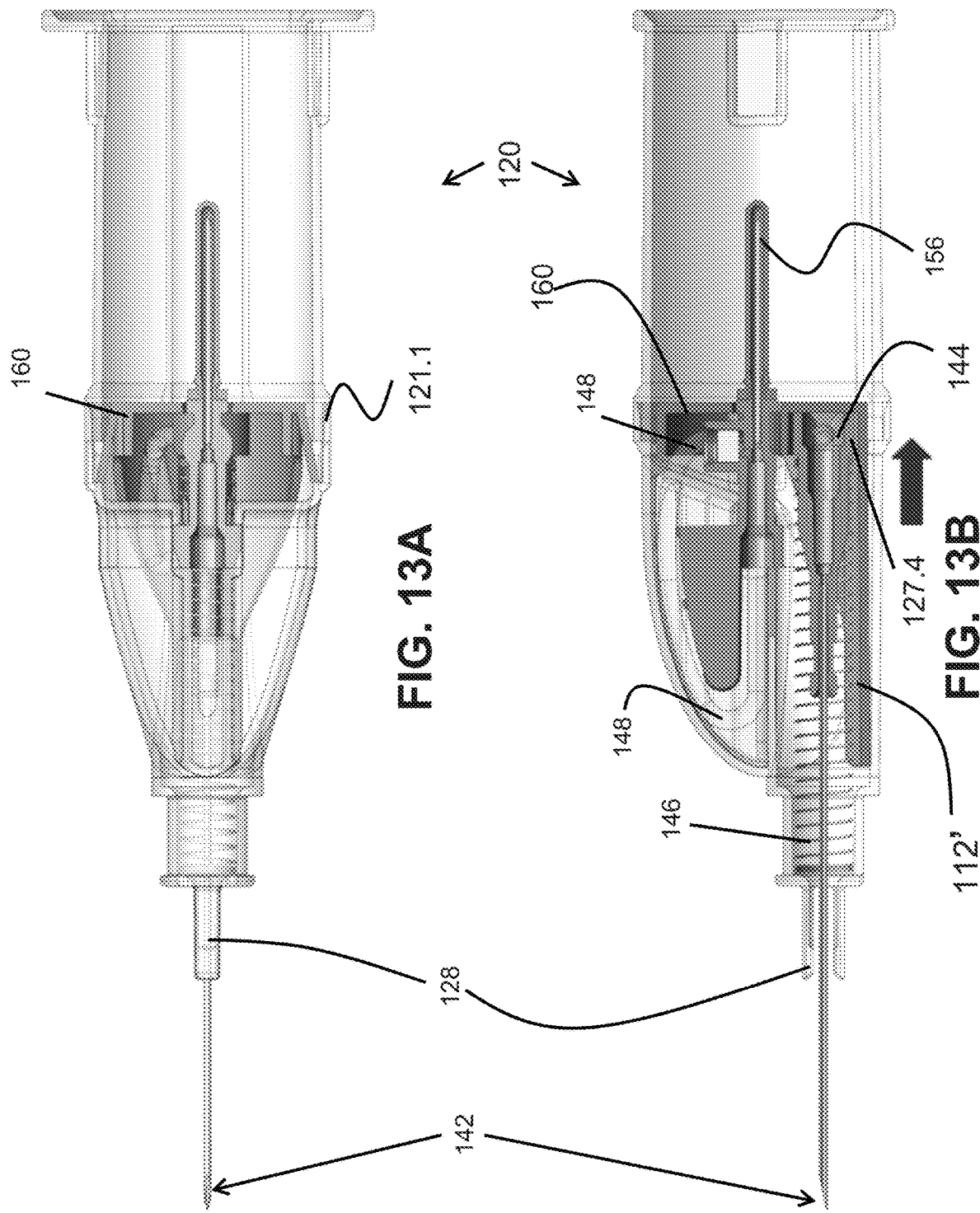

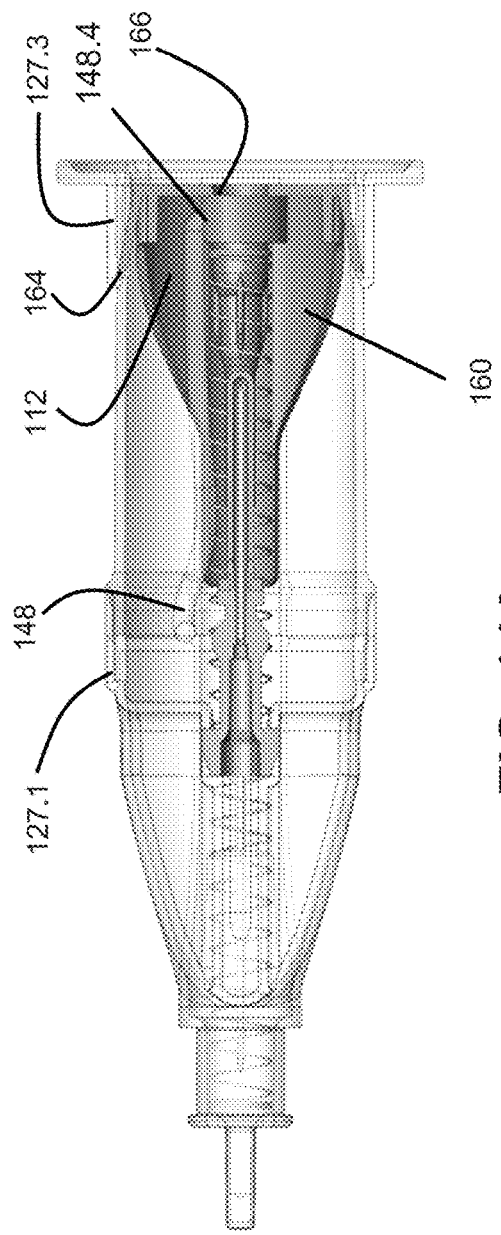
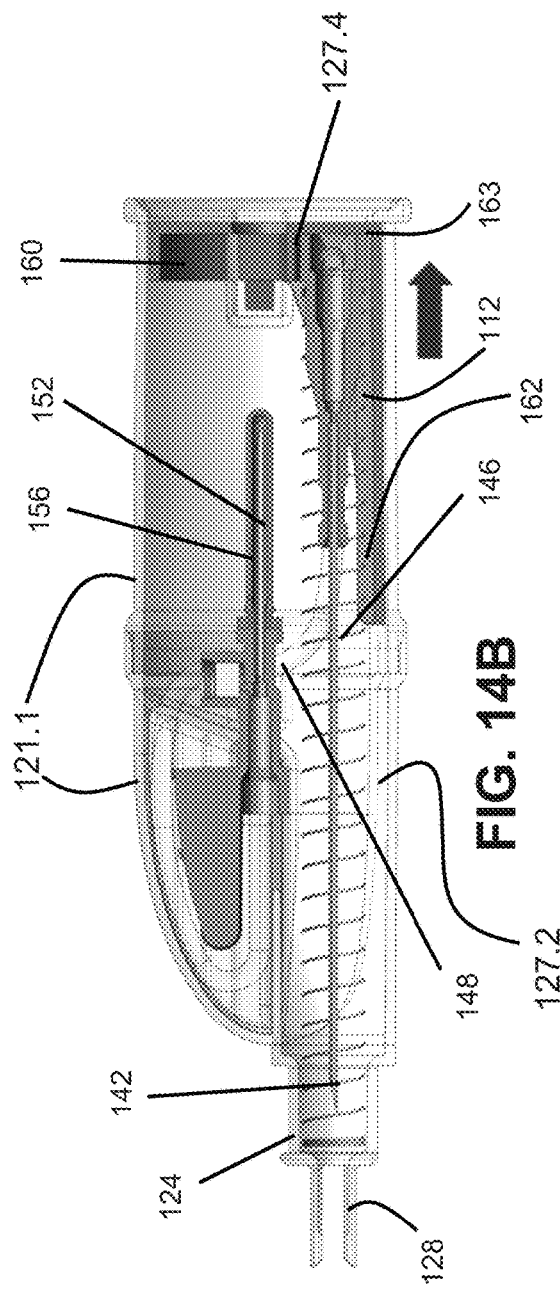
FIG. 14A
FIG. 14B

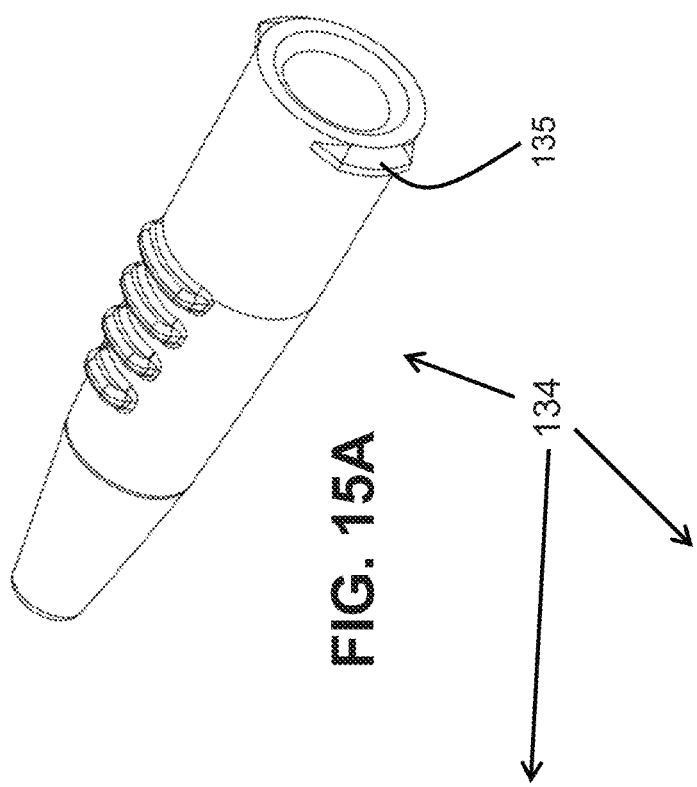
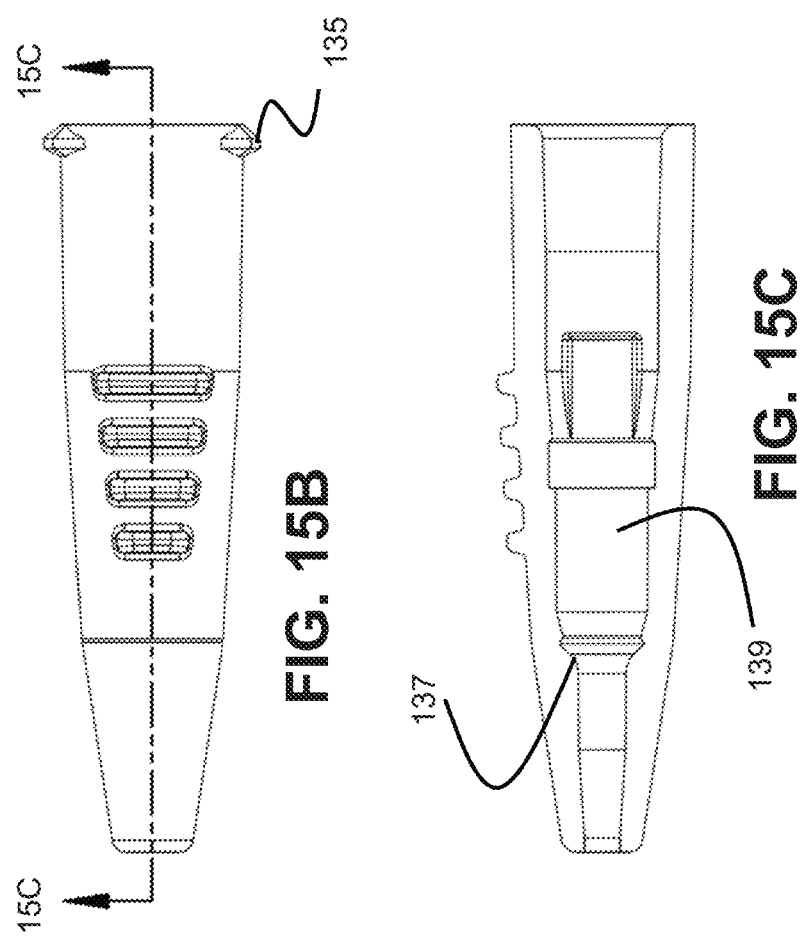
FIG. 15A
FIG. 15B
FIG. 15C

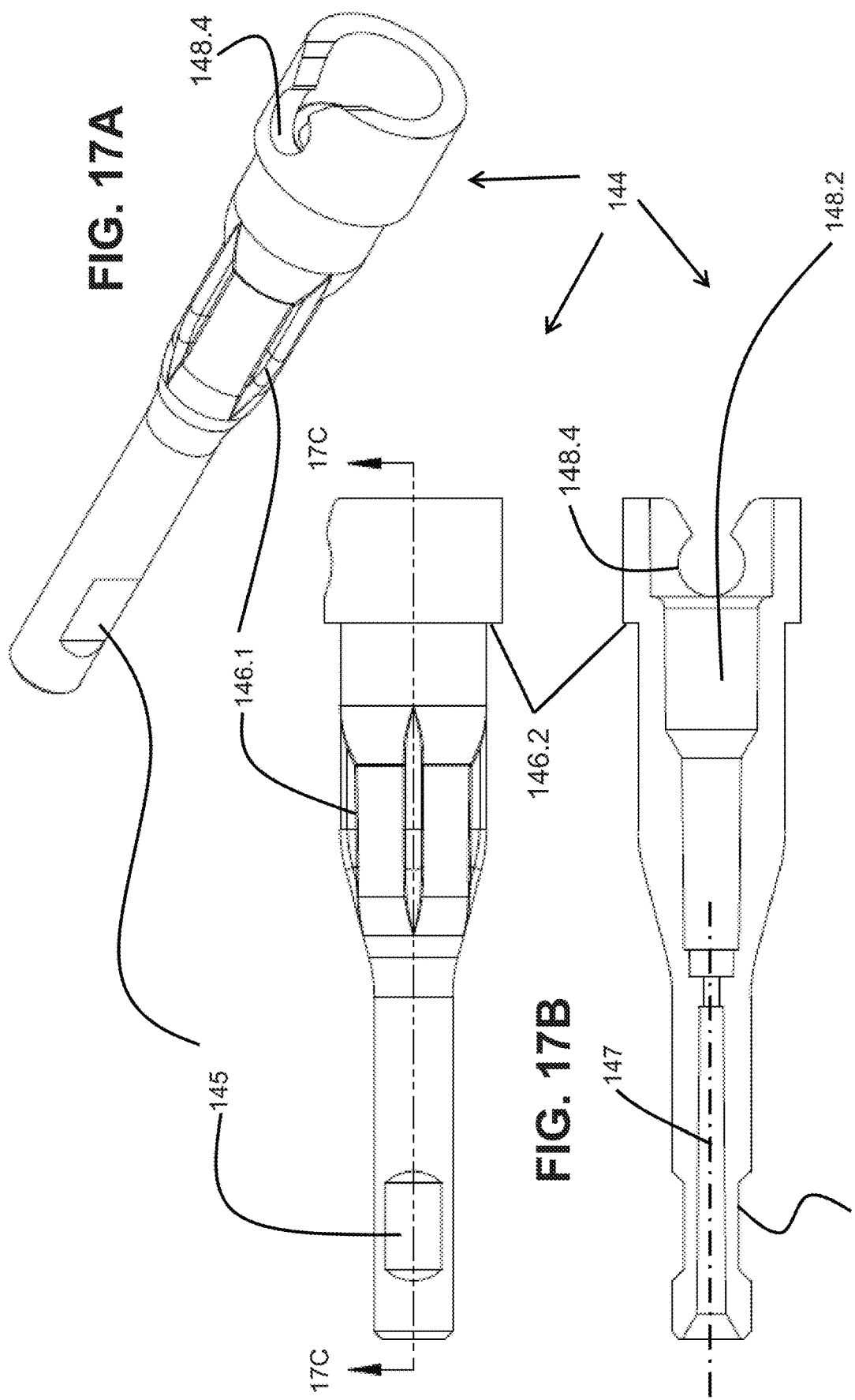

PASSIVE SAFETY I.V. BLOOD COLLECTION CATHETER

CROSS REFERENCE TO RELATED APPLICATION

This application is a continuation of U.S. patent application Ser. No. 14/068,630, filed Oct. 31, 2013, which issued as U.S. Pat. No. 9,456,775 on Oct. 4, 2016, and claims the benefit of priority to U.S. Provisional Patent Application Ser. No. 61/874,771, filed Sep. 6, 2013, all of which are incorporated herein by reference.

FIELD OF THE INVENTION

Various embodiments of the present invention pertain to methods and apparatus for injecting medicaments into a patient and also taking a blood sample from a patient, and including embodiments having a needle retractable to within a guarded chamber after usage.

BACKGROUND OF THE INVENTION

Fluid access into the vasculature of a patient may be necessary for any of several different reasons. Such access may be necessary in order to place medicaments within the patient's circulatory system, or to remove blood or other fluids from the patient for subsequent analysis. For either reason, such access is generally established with the vasculature of the patient, such as a vein. When an infusion protocol is involved that requires periodic injections, an established fluid access site that can be repetitively used for a sequence of different injections may be required. Establishing such an access site, however, can be problematic.

Often, such access is established by a needle extending through the lumen of a catheter, such that both the tip of the needle and the tip of the catheter are located within the patient's vein. The needle is subsequently withdrawn, and the infusion or injections occur after a reservoir and tubing are attached to the luer of the catheter. In yet other situations, it is desirable to obtain blood or other bodily fluid from the patient for subsequent analysis. In such cases the blood may be drawn through a hollow needle inserted into the patient's vasculature or by connection of a blood collection reservoir to an existing, inserted catheter.

Currently, these two functions of introduction of a medicament into the patient, and withdrawal of blood from the patient, are performed in a series of multiple operations by a medical professional, using a plurality of different devices. The current requirement for multiple steps in a procedure using multiple devices provides multiple opportunities for error and multiple risks to the patient. Further, the use of multiple devices requires the clinic administrator to maintain an inventory of many separate devices. Such an inventory is not just expensive, but by itself leads to further risk to the patient if the wrong devices are stocked or used.

Yet further risks are incurred by the medical practitioner, since the devices used for introduction of a medicament or withdrawal of patient blood each can include sharp tipped needles. Since these needles are exposed to the patient's blood, there is a possibility of the medical practitioner being accidentally stuck by a used needle, with the subsequent exposure of the practitioner to the ailment of the patient.

What is needed are devices that address one or more of the aforementioned issues. Various embodiments of the present invention do this in novel and unobvious ways.

SUMMARY OF THE INVENTION

Various aspects of different embodiments of the present invention pertain to the combination of catheter placement for repeat usage, with patient fluid collection at the time of initial placement of the catheter.

Yet other embodiments include aspects directed toward safety features that protect a medical professional from being pierced accidentally by the needle used to introduce the catheter into the patient's circulatory system.

Yet other embodiments include aspects directed toward protection of the medical professional from being accidentally pierced with a needle used to place the patient's blood within a collection vial.

One aspect of the present invention pertains to an apparatus for collecting blood in a container and connecting to intravenous tubing. Some embodiments include a main body including a collection cavity adapted and configured to receive therein an end of a separate container. Other embodiments include a first hollow needle, and a second hollow needle. Still further embodiments include a catheter assembly having a body and a hollow lumen, the catheter body being adapted and configured for attachment to the intravenous tubing. The catheter body includes a one-way valve that prevents flow of blood through the lumen when the first needle is separated from the lumen.

Another aspect of the present invention pertains to an apparatus for collecting blood in a container and connecting to intravenous tubing. Some embodiments include a main body defining an interior including a collection cavity. Other embodiments include a first retractable needle having a first sharp tip, the first needle being movable from a first extended position in which the first sharp tip is exterior to the main body for insertion into a blood vessel to a second retracted position in which the first sharp tip is within the interior. Yet other embodiments include a second needle having a second sharp tip extending into the collection cavity. Still further embodiments include a catheter assembly having a body defining a hollow lumen, the catheter body being adapted and configured for attachment to the intravenous tubing. The first needle and the main body are readily separable from the catheter assembly, the first needle automatically withdrawing to the second position after separating the first needle from the catheter assembly.

Yet another aspect of the present invention pertains to a method for obtaining a sample of blood in a container from the circulatory system of a biological unit. Some embodiments include providing a hand-held device defining an interior including a collection cavity and including first and second hollow needles in fluid communication with each other, and a catheter surrounding the first needle. Yet other embodiments include inserting the first needle and the surrounding catheter into the circulatory system. Still other embodiments include placing the container in the collection cavity and inserting the second needle into the container, either before or after inserting the first needle into the circulatory system. Other embodiments include establishing fluid communication from the first needle to the container, separating the first needle and the catheter; and automatically withdrawing the first needle into the interior by the separating.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting.

FIG. 7 is a cross sectional view of the apparatus of FIG. 2 in a third mode of operation.

FIG. 8 is a cross sectional view of the apparatus of FIG. 2 in a final, used position, and ready for disposal.

FIG. 9A shows a top plan view of an apparatus according to another embodiment of the present invention.

FIG. 9B shows a side elevational view of the apparatus of FIG. 9A.

FIG. 11A is a top, partially see-thru CAD representation of the embodiment of FIG. 10, assembled, and in a first mode of operation.

FIG. 11B is a side elevational cross-sectional view of the apparatus of FIG. 11A.

FIG. 12A is a top, partially see-thru CAD representation of the embodiment of FIG. 10, assembled, and in a second mode of operation.

FIG. 12B is a side elevational cross-sectional view of the apparatus of FIG. 12A.

FIG. 13A is a top, partially see-thru CAD representation of a portion of the embodiment of FIG. 10, assembled, and in a third mode of operation.

FIG. 13B is a side elevational cross-sectional view of the apparatus of FIG. 13A.

FIG. 14A is a top, partially see-thru CAD representation of the embodiment of FIG. 10, assembled, and in a final, used position, and ready for disposal.

FIG. 14B is a side elevational cross-sectional view of the apparatus of FIG. 14A.

FIGS. 15A, 15B, and 15C are top perspective, top plan, and cross sectional line drawings, respectively, of the luer body of FIG. 10.

FIGS. 17A, 17B, and 17C are top rear, side elevational, and cross sectional line drawings, respectively, of a portion of the needle assembly of FIG. 10.

ELEMENT NUMBERING

Figure 1:
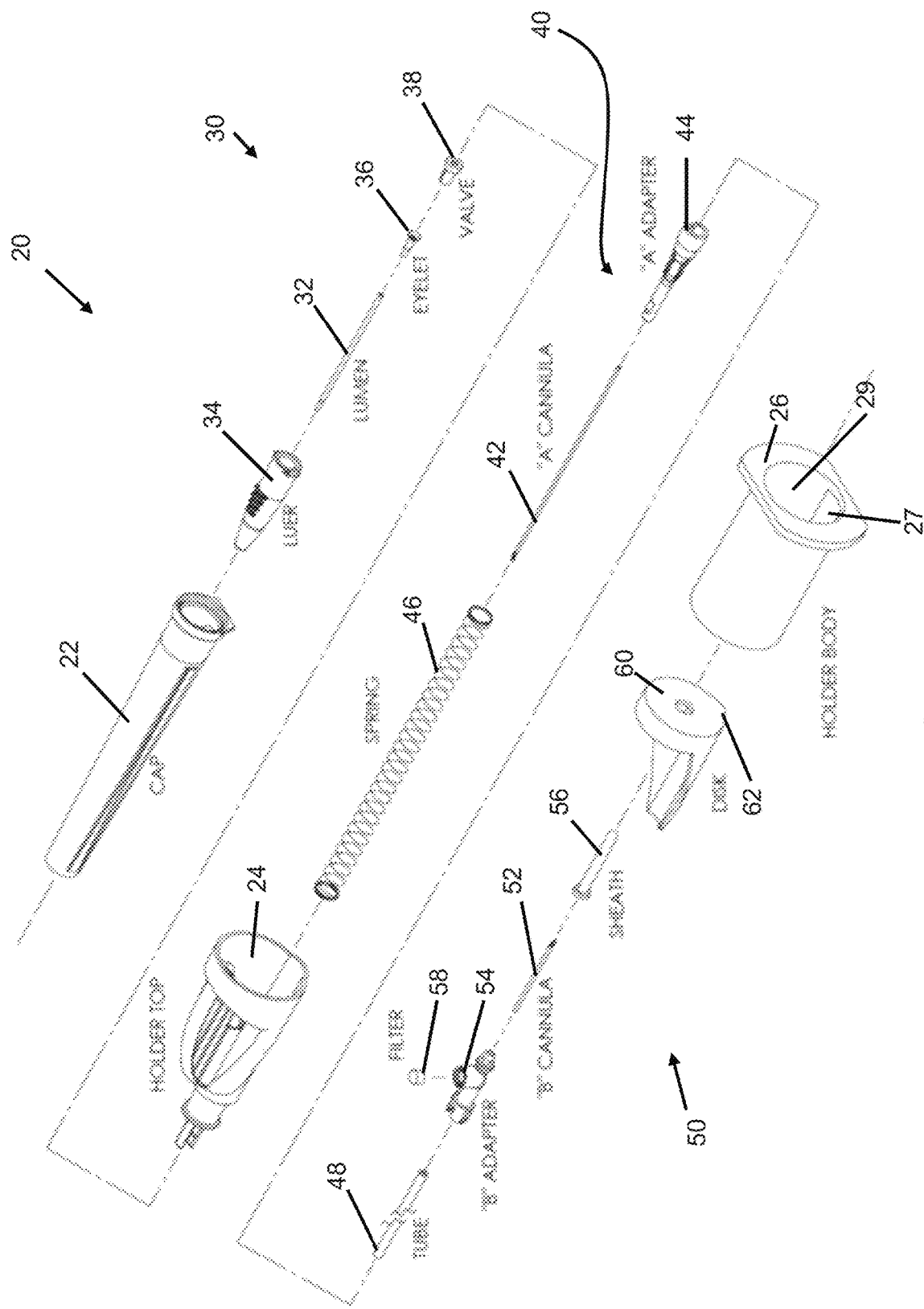
FIG. 1 is a perspective, exploded line drawing of an apparatus according to one embodiment of the present invention.

The following is a list of element numbers and at least one noun used to describe that element. It is understood that none of the embodiments disclosed herein are limited to these nouns, and these element numbers can further include other words that would be understood by a person of ordinary skill reading and reviewing this disclosure in its entirety.

| | |
|---|---|
| 10 | collection vessel |
| 11 | first position |
| 12' | movement toward second position |
| 12 | second position |
| 20 | apparatus |
| 21.1 | main body |
| 21.2 | collection cavity |
| 22 | cap |
| 24 | holder top |
| .1 | collection valve guide |
| .2 | collection valve slot |
| 25 | window |
| 26 | holder body |
| 27 | cylindrical receptaclel; wall |
| .1 | distal guide and stop; groove |
| .2 | $2^{nd}$ complementary feature |
| .3 | proximal guide and stop; groove |
| .4 | pocket |
| 28 | fingers |
| 29 | collector aperture |
| 30 | IV catheter assy |
| 32 | flexible lumen |
| 34 | luer body |
| 35 | locking feature |
| 36 | eyelet |
| 37 | eyelet receptacle |
| 38 | valve, 1-way or 2-way |
| 39 | valve receptacle |

-continued

| | |
|---|---|
| 40 | needle assembly |
| 42 | cannula, sharp tipped |
| 44 | a adapter |
| 45 | flat or flattened area; groove |
| 46 | spring |
| .1 | spring guide |
| .2 | ridges |
| .3 | recess |
| 47 | centerline; axis |
| 48 | tube |
| .1 | tube guide |
| .2 | tube port |
| .3 | tube port |
| .4 | tube holder |
| 50 | collection valve assy. |
| 51 | locking tabs; guiding ear |
| 52 | cannula |
| 54 | b adapter body |
| 55 | body guided member |
| 56 | sheath |
| .1 | sheath coupling |
| 57 | centerline; axis |
| 58 | filter |
| 59 | filter receptacle |
| 60 | sliding disk member |
| 61 | leg |
| 62 | protrusion; 1$^{st}$ complementary feature |
| 63 | cover |
| 64 | flexible hinge member; ear |
| 65 | shoulder wings |
| 66 | cannula aperture |

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "preferably," refers to features and aspects that are present in at least one embodiment, but which are optional for some embodiments.

The use of an N-series prefix for an element number (NXX.XX) refers to an element that is the same as the non-prefixed element (XX.XX) except as shown and described. As an example, an element 1020.1 would be the same as element 20.1, except for those different features of element 1020.1 shown and described. Further, common elements and common features of related elements may be drawn in the same manner in different figures, and/or use the same symbology in different figures. As such, it is not necessary to describe the features of 1020.1 and 20.1 that are the same, since these common features are apparent to a person of ordinary skill in the related field of technology. Further, it is understood that the features 1020.1 and 20.1 may be backward compatible, such that a feature (NXX.XX) may include features compatible with other various embodiments (MXX.XX), as would be understood by those of ordinary skill in the art. This description convention also applies to the use of prime ('), double prime ("), and triple prime ("') suffixed element numbers. Therefore, it is not necessary to describe the features of 20.1, 20.1', 20.1", and 20.1"' that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

Various references may be made to one or more processes, algorithms, operational methods, or logic, accompanied by a diagram showing such organized in a particular sequence. It is understood that the order of such a sequence is by example only, and is not intended to be limiting on any embodiment of the invention.

This document may use different words to describe the same element number, or refer to an element number in a specific family of features (NXX.XX). It is understood that such multiple usage is not intended to provide a redefinition of any term herein. It is understood that such words demonstrate that the particular feature can be considered in various linguistical ways, such ways further not necessarily being additive or exclusive.

Various embodiments of the invention disclosed herein combine the basic elements of both an IV catheter and a blood collector and then expands upon those features resulting in a fully automatic/passive safety product that seamlessly shields the user against needle stick injuries in one simple step. Immediately upon separation of the catheter luer from the main body, both cannula sharps are simultaneously and automatically shielded within the collection holder. This renders the device unusable and safe for proper disposal. As used herein, the term "proximal" refers to proximity to the user, and with regards to FIG. 2 or 9, to the right of the drawing. The word "distal" refers to a direction generally opposite of the proximal direction FIG. 1 presents an exploded view of an apparatus 20 according to one embodiment of the present invention. Apparatus 20 provides a single device that can be used as part of a catheter for the intravenous delivery of medicaments, but also provide an interface through which the patient's blood can be collected. In still further embodiments, the apparatus includes a needle that is useful for puncturing a vein of a patient, and also for providing a flow of the patient's blood into a separate collection vessel such as a standard collection tube (not shown).

FIG. 1 shows an apparatus 20 having an IV catheter 30, needle assembly 40, collection valve 50, and latching disk 60. The catheter 30, needle 40, valve 50, and disk 60 are contained within a cap 22, holder top 24, and holder body 26.

Figure 2:
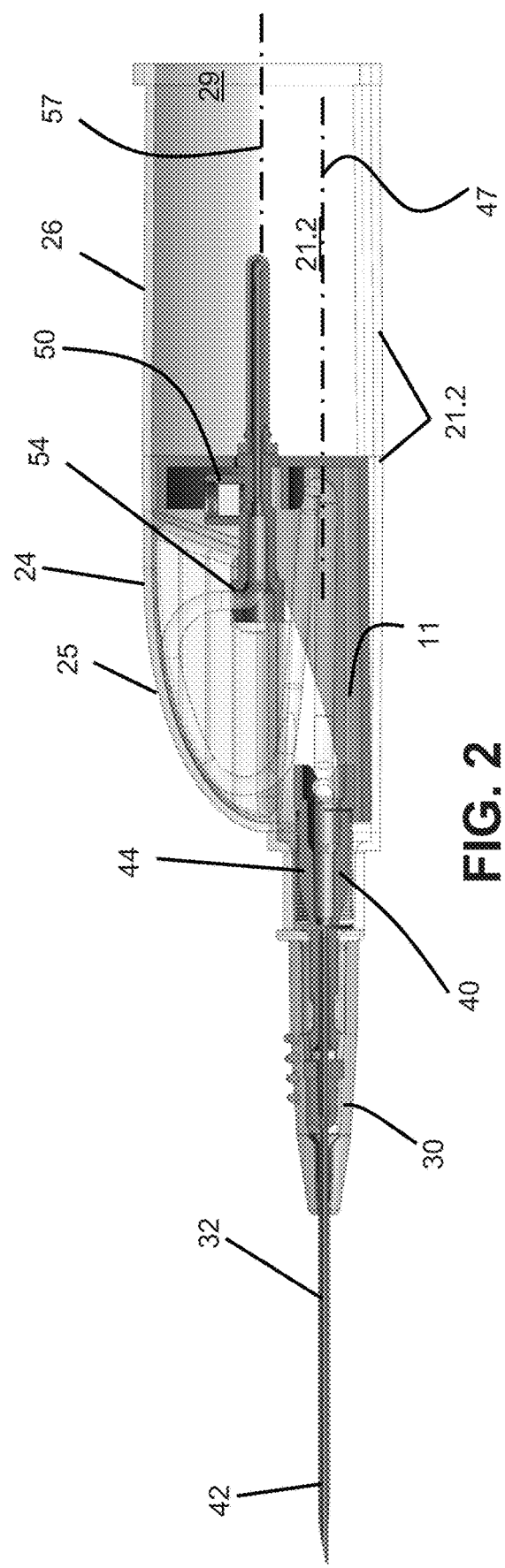
FIG. 2 is a cross sectional view of the apparatus of FIG. 1, as represented with a drawing from a shaded CAD model, and in a first mode of operation.
Figure 3:
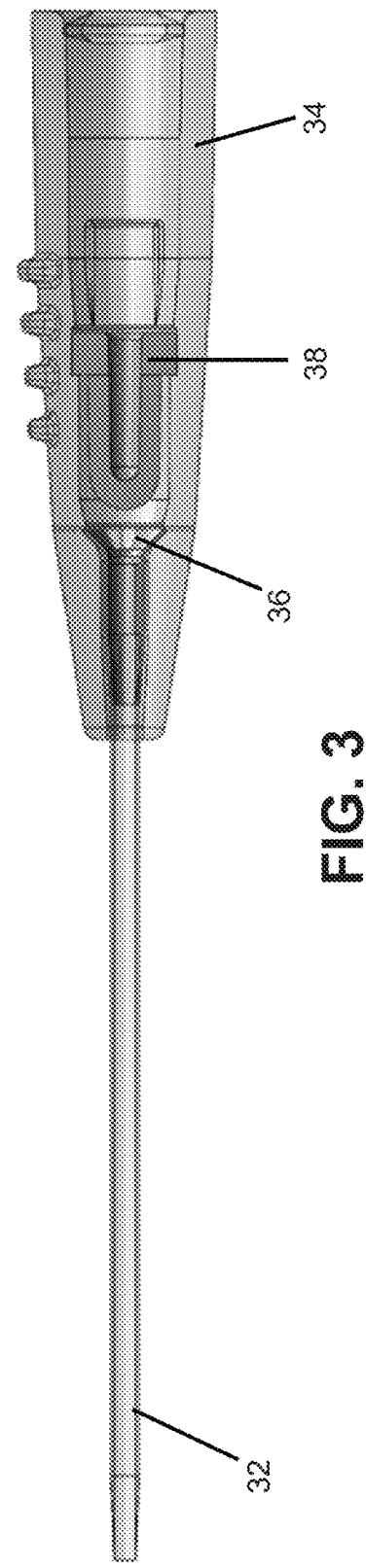
FIG. 3 is a cross sectional representation of a portion of the apparatus of FIG. 2.

Apparatus 20 can be seen in a side elevational cross sectional view in FIG. 2. The holder top 24 and holder body 26 in one embodiment are molded plastic pieces that are joined together by any suitable process, including as examples, by way of snap fit, by adhering with a glue, by ultrasonic welding, or the like. Although holder top 24 and holder body 26 are shown as two separate pieces, it is understood that various embodiments of the present invention contemplate these two components being combined into a single main body 21.1, and still further contemplates those other embodiments in which the various structural features of holder top 24 and holder body 26 are redistributed among two or more different separate pieces, but which still function as a main body 21.1 when assembled. The catheter assembly 30, needle assembly 40, and collection valve assembly 50 are all preferably supported by the holder top 24, as will be described.

FIG. 2 shows a view of apparatus 20 in which protective cap 22 has been removed. It is understood that cap 22 provides for safe handling of the sterile, exposed needle 42 and catheter 32 during storage and handling. The opened proximal end of cap 22 fits over the distal-most end of holder top 24 in a manner that provides not only for safe handling and storage, but also for easy, ready removal by a medical professional. Preferably, cap 22 covers lumen 32 and luer 34.

Placed on the distal-most end of holder top 24 is an intravenous catheter assembly 30. Assembly 30 includes a hollow luer body 34 that includes a flexible lumen 32 extending in a distal-direction. Lumen 32 is preferably attached to an inner surface of luer body 34 by way of an eyelet 36. Luer body 34 also supports an internal one-way valve 38 that is located generally in the middle of the length of body 34. In some embodiments, valve 38 is a 1-way valve, whereas in other embodiments it is a 2-way valve. Preferably, valve 38 permits cannula 42 to be extended through the valve dome, without leakage. Upon withdrawal of cannula 42, the dome of valve 38 substantially seals to a fluid-tight state.

Figure 4:
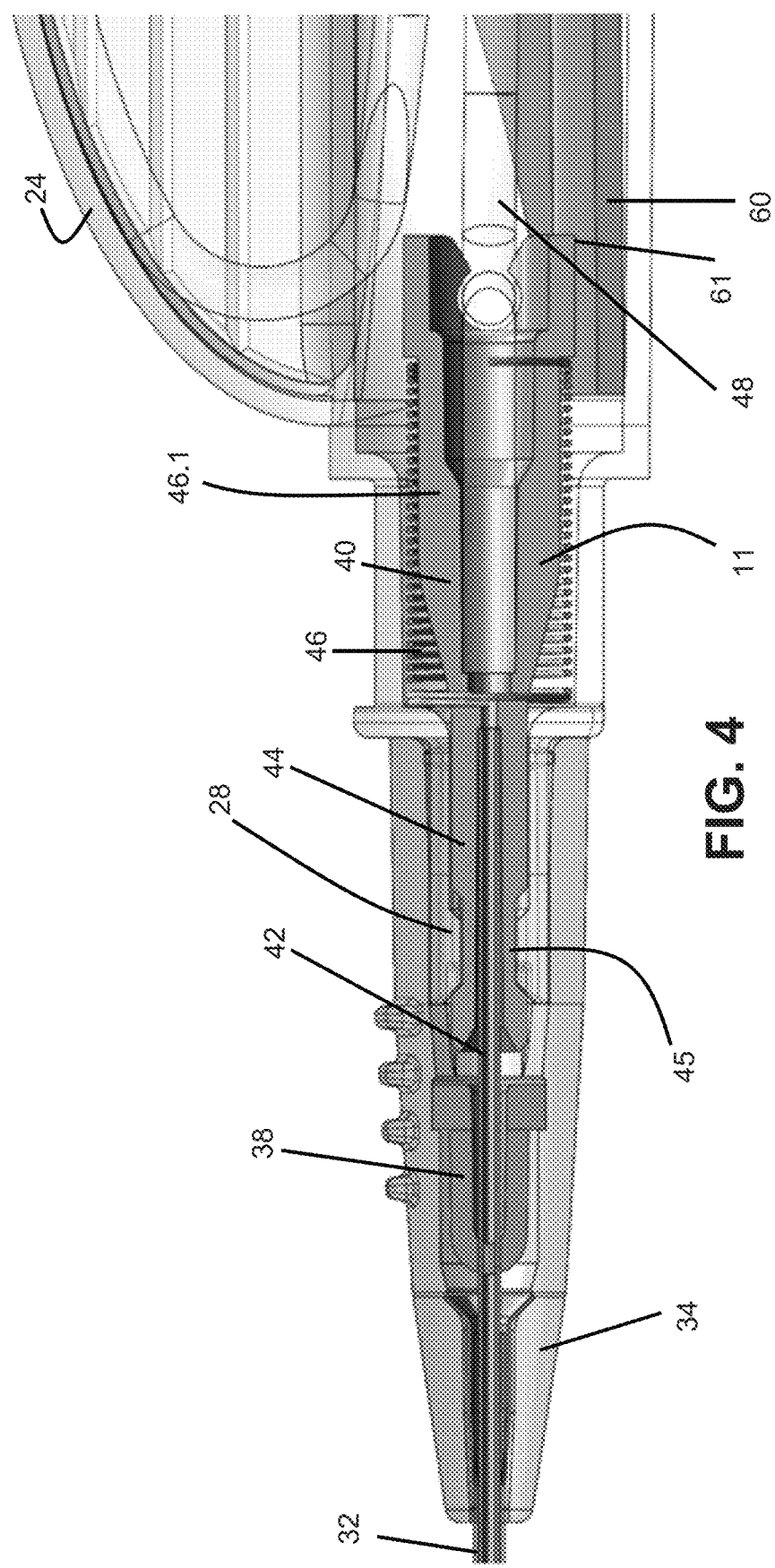
FIG. 4 is an enlarged cross section of a portion of the apparatus of FIG. 2.

The proximal end of body 34 includes an inner diameter that establishes a friction fit over a pair of forward-extending fingers 28 that are part of holder top 24 (shown in FIG. 4). In some embodiments, luer body 34 also includes a plurality of ridges on one or more outer surfaces that assist the medical practitioner in handling of catheter assembly 30.

FIGS. 2 and 4 include cross sectional views of a needle assembly 40. Needle assembly 40 preferably includes a beveled, sharp-tipped needle 42 that is fixed to the internal surfaces of a shuttling adapter 44. Cannula 42 is adapted and configured to extend within flexible lumen 32 of catheter 30. The tip of cannula 42 extends beyond the end of flexible lumen 32. During insertion of needle 42 and lumen 32 into the vein of a patient, needle 42 provides a stiffening function that maintains the cylindrical shape of lumen 32, preventing buckling of lumen 32 during insertion of the needle 42 and catheter 30 into the vein of the patient.

As best seen in FIG. 4, needle assembly 40 further includes a spring 46 that is located between opposing, facing shoulders of adapter 44 and holder top 24. FIG. 4 shows needle assembly 40 inserted fully within catheter assembly 30, with the resultant maximum compression of spring 46. Preferably, spring 46 is a coil spring, although it is appreciated that various devices and methods can be used to bias apart adapter 44 and the forward shoulder of holder top 24.

It can also be seen in FIG. 4 that cannula 42 extends through the distal-most end of valve 38, and thus provides fluid communication from the tip end aperture of needle 42, to the proximal-most opened end of adapter body 44.

Referring to FIG. 4, a disk leg 61 operating as a guide for adapter 44 can be seen (leg 61 preferably not being engaged with adapter 44). A first latching mechanism between disk 60 and holder top 24 establishes the relative locations of needle assembly 40 and disk 60. A second latching mechanism establishes the relative positions of disk 60 and holder body 26. Disk 60 sits in a relaxed position between the holder top and holder body with a slight interference fit. In a manner that will be described later, leg 61 of disk 60 maintains radial alignment within the holder body 24 and acts as a guide to needle assembly 40 in a forwardmost position, with spring 46 under near-maximum compression, during a first mode of operation of apparatus 20.

Figure 5:
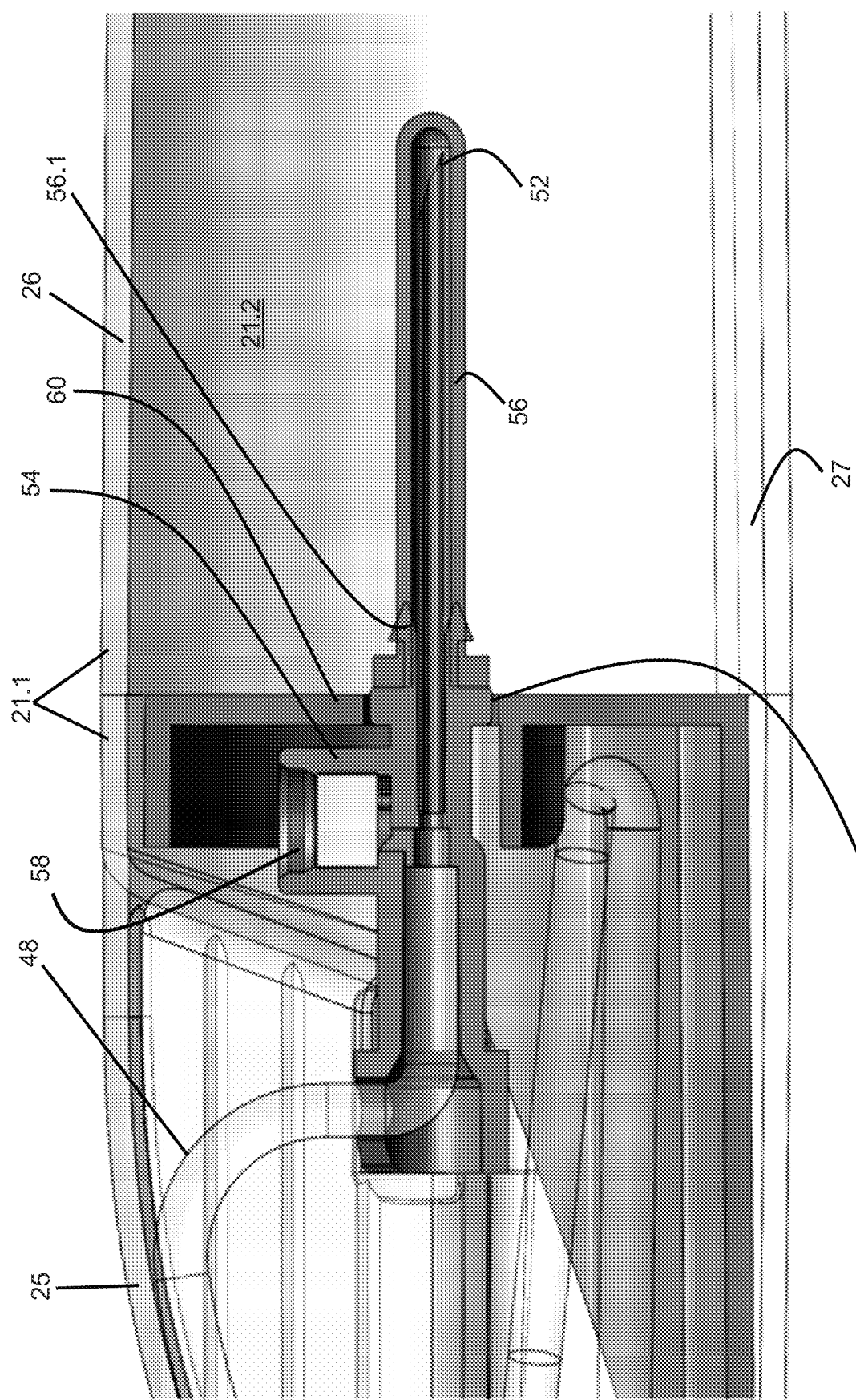
FIG. 5 is an enlarged cross section of a portion of the apparatus of FIG. 2.

FIG. 5 shows an enlarged sectional view of a portion of apparatus 20. A latching disk 60 can be seen located within a generally cylindrical aperture 29 of holder body 26. Disk 60 is preferably a single, molded piece having a forwardly-extending leg. Various features of disk 60 are adapted and configured to provide a first latching between disk 60 and retractable needle assembly 40, and a second latching between disk 60 and either holder top 24 or holder body 26.

Collection valve assembly 50 is attached to internal support ribs of holder top 24. Disk 60 includes a small, central aperture that loosely fits around an outer diameter of a shoulder of adapter 54. Thus, disk assembly 60 is free to move relative to adapter body 54, and body 54 is held fixed by holder top 24. A flexible tube 48 provides fluid communication from adapter 44 and cannula 42 to one end of adapter body 54.

Referring briefly to FIG. 2, it can be seen that adapter 54 establishes a centerline 57 generally within the center of chamber 21.2 of holder body 26. Adapter body 44 and cannula 42 establish a second centerline 47 that is generally parallel to, and offset from, centerline 57. However, it is understood that yet other embodiments of the present invention contemplate relative arrangements of the centerlines of needle assembly 40 and collection valve assembly 50, including non-parallel arrangements (in which centerline 57 and aperture 29 of holder body 26 would be angled upward, away from the patient, referring to FIG. 2) and also those embodiments in which centerlines 47 and 57 are not offset (such as when the two axes are generally aligned).

Referring again to FIG. 5, it can be seen that adapter 54 supports a cannula 52 that extends rearward toward the proximal opening 29 of holder body 26. A conical barb at the proximal end of adapter body 54 further support a flexible sheath 56 that generally surrounds and seals cannula 52 to adapter body 54. Preferably, sheath 56 is fabricated from a flexible material, such as a silicone rubber, and can therefore easily be compressed and collapsed around cannula 52. The proximal-most end of cannula 52 preferable includes a beveled, sharp tip for puncturing a collection vessel, as will be described later.

Figure 6:
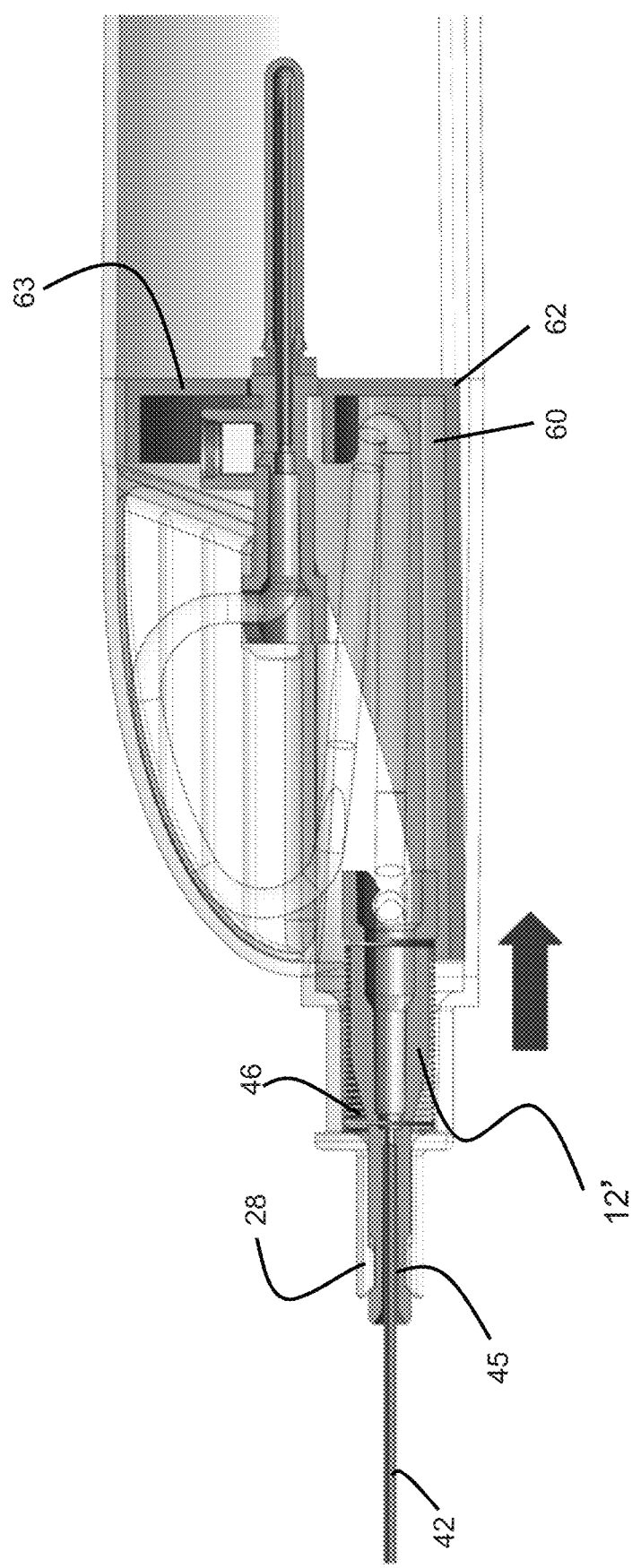
FIG. 6 is a cross sectional view of the apparatus of FIG. 2 in a second mode of operation.

FIG. 5 further shows that adapter body 54 supports a porous filter 58 that provides a purging function for the interior volume of cannula 42, adapter body 44, tube 48, and adapter body 54. The proximal end of disk 60 includes a protrusion 62 that is shown in FIG. 6 as being held against a forward ledge of holder body 26.

Apparatus 20 operates in several different modes. FIG. 1 is an exploded view of a storage mode of operation, in which catheter assembly 30 is located at the distal-most end of holder top 24, with full compression of spring 46. Further, in this storage mode, sheath 56 is unpunctured, and maintains the sterility of the internal flowpath of assembly 20.

FIG. 2 represents apparatus 20 in a first mode of operation. Cap 22 has been removed, exposing the sharp tip of cannula 42 and the exterior of flexible lumen 32. The medical practitioner has access to hold the exterior of luer body 34, as well as the ability to hold the exterior of holder top 24 and holder body 26. The medical practitioner places the sharp tip of cannula 40 relative to a vein of a patient, and inserts the cannula 42 and flexible lumen 32 within the vein of the patient.

In a second mode of operation, the medical practitioner can bring a standard collection vessel 10 (not shown) through aperture 29 and into the opened proximal chamber 21.2 of holder body 26. The proximal end of body 26 includes a generally cylindrical chamber 21.2. The interior dimensions of the proximal end of holder body 26 are slightly greater than the outer diameter of the collection vessel. Therefore, the collection vessel enters aperture 29, and the face of the collection vessel can be brought into contact with the proximal end of sheath 56.

Preferably, the end of the collection vessel 10 is soft enough such that the medical practitioner can push the collection vessel against sheath 56 and the sharp tip of cannula 52. By continuing to push the collection vessel toward adapter 54, the sharp tip of cannula 52 penetrates the end of collection vessel 10, and enters the interior of the collection vessel. However, the flexible sheath 56 does not enter the collection vessel, and instead is compressed in buckling along cannula 52 and toward adapter body 54.

Once the tip of cannula 52 extends within the empty volume of collection vessel 10, fluid communication is established from the interior of the collection vessel through cannula 52 and adapter body 54, through tube 48, and into the interior flow passage of needle assembly 40. Since needle assembly 40 is exposed to blood within the patient's vein, blood can begin to flow through needle assembly 40 and tube 48, through collection valve assembly 50, and into collection vessel 10.

In order to prevent any hydraulic lockup, the interior of collection vessel 10 can be established at a pressure less than the pressure of the blood within the vein, or a suitable fluid induction device can be used. Still further, any trapped air within needle assembly 40, tube 48, and valve assembly 50 can escape through porous filter 58. However, filter 58 is preferably of a type in which the porosity of the filter is maintained only so long as the filter does not contact blood (such as a Porex® material). Upon contact with the blood, the filter media loses porosity, such that there can be no further leakage of either trapped air or blood through the filter. As blood flows through tube 48, it can be seen by the medical practitioner through a transparent window 25 within holder top 24.

The medical practitioner maintains collection vessel 10 within holder body 26 and in fluid communication with the vein of the patient until sufficient blood has been collected. Multiple collection vials maybe used. After the medical professional has collected sufficient blood, the compression is relieved and the collection vessel 10 is withdrawn. The adapter 44 assembly still remains in a distal position, under spring load, until the luer assembly 30 has separated from the Holder Top 24. The relationship between the luer body 34, holder top legs 28 and adapter 44 receiving flats 45 prevent movement. Once the user advances the catheter luer assembly in a distal direction beyond legs 28, there is nothing to prevent them from flexing outward. This outward flexing releases adapter 44 so it can move in a proximal direction, retracting toward the proximal end of holder body 26. Needle assembly 40 can move rearward toward a receiving pocket on the end of disk 60. Both disk 60 and needle assembly 40 therefore move toward the proximal end of the body holder. The beginnings of this movement can be first seen in FIG. 6. The full seating of the needle assembly in the receiving pocket of disk 60 can be seen in FIG. 7 Cannula 42 of needle assembly 40 retracts within flexible lumen 32 of catheter assembly 30. However, the medical practitioner advances the catheter assembly 30 into the patient's vein, with the result that lumen 32 remains in fluid communication with the patient's vein. However, as needle assembly 40 retracts, the end of the needle assembly retracts past flexible valve 38, which acts as a one-way valve, and thereby closes and prevents any escape of the patient's blood.

FIGS. 7 and 8 show the remaining retraction of needle assembly 40 within holder body 26. As the assembly of the disk and needle retract, tube 48 begins to extend. FIG. 7 shows the completed and full retraction of needle assembly 40 relative to disk 60. FIG. 8 shows the completed and full retraction of the disk relative to holder 26. The aft face of disk 60 is biased by spring 46 to sit against a ledge or shoulder surrounding aperture 29 of holder body 26 and locks into place preventing any further movement. Tube 48 is shown in its position of maximum extension from the end of adapter 44 to the end of adapter 54. The sharp tip of cannula 42 is fully contained within holder top 24.

In some embodiments, the relationship between adapter 44 and disk 60 is generally for guiding disk 60 to its full proximal position. Various embodiments do not include features that pre-stage activation upon insertion of a collection Tube 10. The disk 60 statically stays positioned in the holder top 24 by a simple interference fit having a reverse draft. Multiple collection tubes can be used without activation since activation (retraction of the needle assembly 40 and disk 60) does not occur until the catheter luer assembly 30 has separated from the holder 24.

FIGS. 9-20 pertain to an apparatus 120 according to another embodiment of the present invention. FIG. 9A and FIG. 9B show top and side external views, respectively, of device 120. A main body 121.1 has a protective cap 122 on one end, and an aperture 129 defined on the opposite end, the aperture being adapted and configured to accept a collection vessel. Although what will be shown and described is an embodiment configured to accept a vessel such as an evacuated, cylindrical vessel, the present invention further contemplates those embodiments in which the aperture is adapted and configured to accept any shape, size, or type of collection vessel, and further included those embodiments adapted and configured to accept tubing-like components that are in fluid communication with a collection reservoir.

Figure 10:
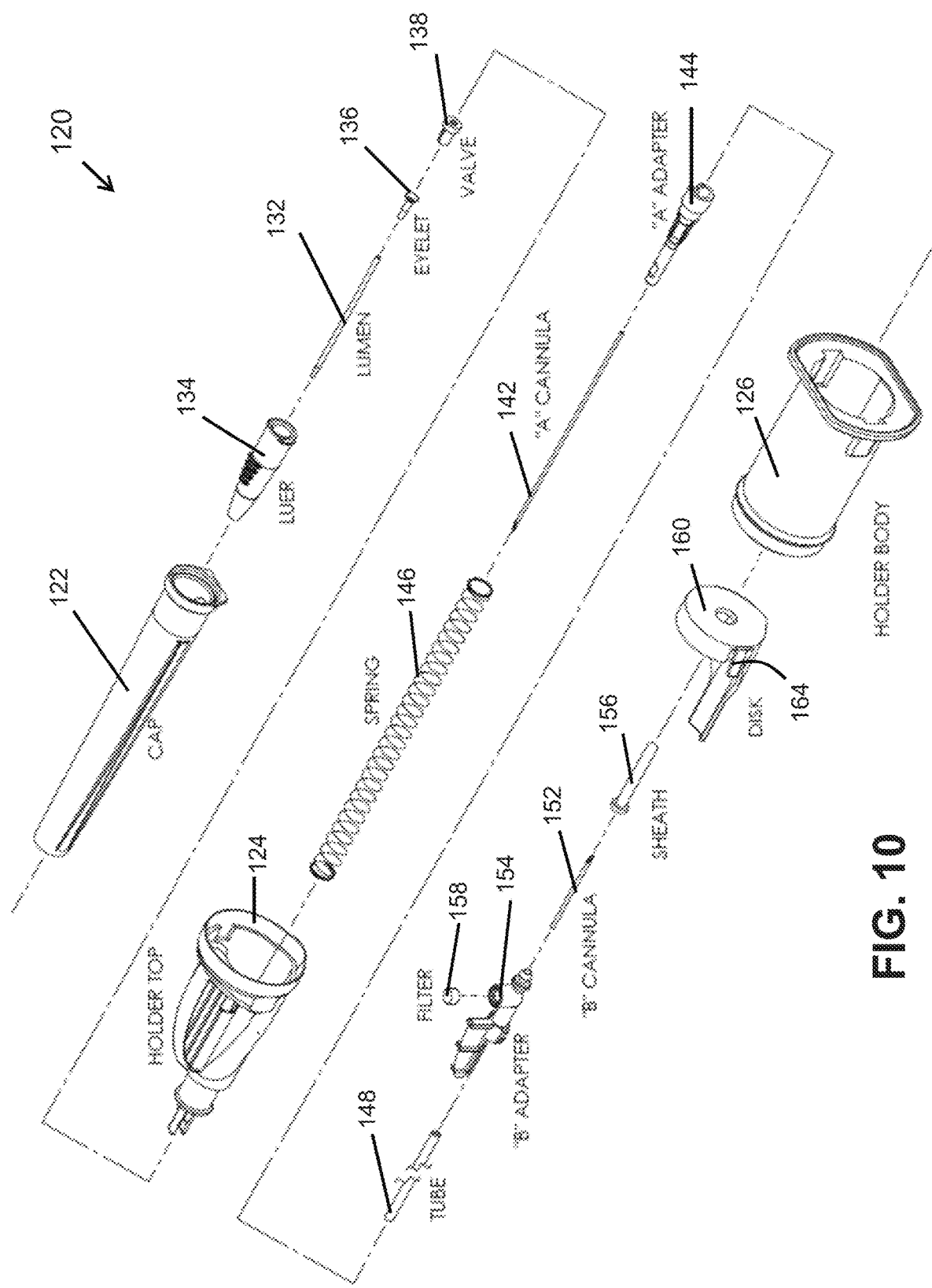
FIG. 10 is a perspective, exploded line drawing of the device of FIG. 9.

FIG. 10 presents an exploded view of an apparatus 120 according to one embodiment of the present invention. Apparatus 120 provides a single device that can be used as part of a catheter for the intravenous delivery of medicaments, but also provide an interface through which the patient's blood can be collected. In still further embodiments, the apparatus includes a needle that is useful for puncturing a vein of a patient, and also for providing a flow of the patient's blood into a separate collection vessel such as a standard collection tube (not shown).

FIG. 10 shows an apparatus 120 having an IV catheter 130, needle assembly 140, collection valve 150, and latching disk 160. The catheter 130, needle 140, valve 150, and disk 160 are contained within a cap 122, holder top 124, and holder body 126.

Apparatus 120 can be seen in a top elevational view in FIG. 11A and a side elevational cross sectional view (taken along the centerline of FIG. 11A) in FIG. 11B. The holder top 124 and holder body 126 in one embodiment are molded plastic pieces that are joined together by any suitable process, including as examples, by way of snap fit, by adhering with a glue, by ultrasonic welding, or the like. The catheter assembly 130, needle assembly 140, and collection valve assembly 150 are all preferably supported by the holder top 124, as will be described.

FIGS. 11A and 11B show views of apparatus 120 in which protective cap 122 has been removed. It is understood that cap 122 provides for safe handling of the sterile, exposed needle 142 and catheter 132 during storage and handling. The opened proximal end of cap 122 fits over the distal-most end of holder top 124 in a manner that provides not only for safe handling and storage, but also for easy, ready removal by a medical professional. Preferably, cap 122 covers lumen 132 and luer body 134, and the tip of cannula 142.

Placed on the distal-most end of holder top 124 is an intravenous catheter assembly 130. Assembly 130 includes a hollow luer body 134 that includes a flexible lumen 132 extending in a distal-direction. Lumen 132 is preferably attached to an inner surface of luer body 134 by way of an eyelet 136. Luer body 134 also supports an internal valve 138 within a receptacle 139 that is located generally in the middle of the length of body 134 (luer body 134 also being shown in FIG. 15). The proximal end of body 134 includes an inner diameter that establishes a friction fit over a pair of forward-extending fingers 128 that are part of holder top 124 (also shown in FIGS. 14A and 14B). In some embodiments, luer body 134 also includes a plurality of ridges on one or more outer surfaces that assist the medical practitioner in handling of catheter assembly 130. The placement of luer body 134 over fingers 128 causes the tips of these fingers to be pressed firmly within corresponding flats 145 of body 144 (as seen in FIG. 17). The inner surface of luer body 134 fits over fingers 128 and compresses them into flats 145 so as to firmly hold needle assembly 140 in place, and able to resist a force exerted on needle assembly 140 by spring 146 (as will be discussed later). Luer body 134 includes one or more locking features 135 that are adapted and configured for connection to another medical device.

FIG. 16 show various views of a portion of a main body according to one embodiment of the present invention. In this embodiment, the main body includes a holder top 124 that provides a variety of functions with a variety of different features. These functions and features will be described, but it is understood that the present invention contemplates those embodiments in which one or more of these functions and features are not included.

Holder top 124 includes a distal end having a pair of distally extending fingers 128 that provide for capture of needle assembly 140 as discussed herein. The proximal end of holder top 124 defines an aperture that is adapted and configured to receive therein the distal end of the holder body 126. Further, the open proximal end of holder top 124 includes a pair of distal guide/stop grooves 127.1 arranged on generally opposite sides. These grooves 127.1 coact with corresponding ears 164 of sliding disk member 160 as will be described later. The open end of holder top 124 further includes a guiding feature 127.2 that is generally complementary in shape to a corresponding guiding feature 162 of sliding disk member 160, as will be discussed later.

Holder top 124 includes an outer shape adapted and configured to provide a hand hold for the medical professional. As best seen in FIG. 16B, holder top 124 has a width that decreases in the distal direction, and further has a height that decreases in the distal direction. This curving shape, which reduces from proximal to distal end, provides a secure hold of apparatus 120 within the hand and fingers of a medical professional.

Figure 18A:
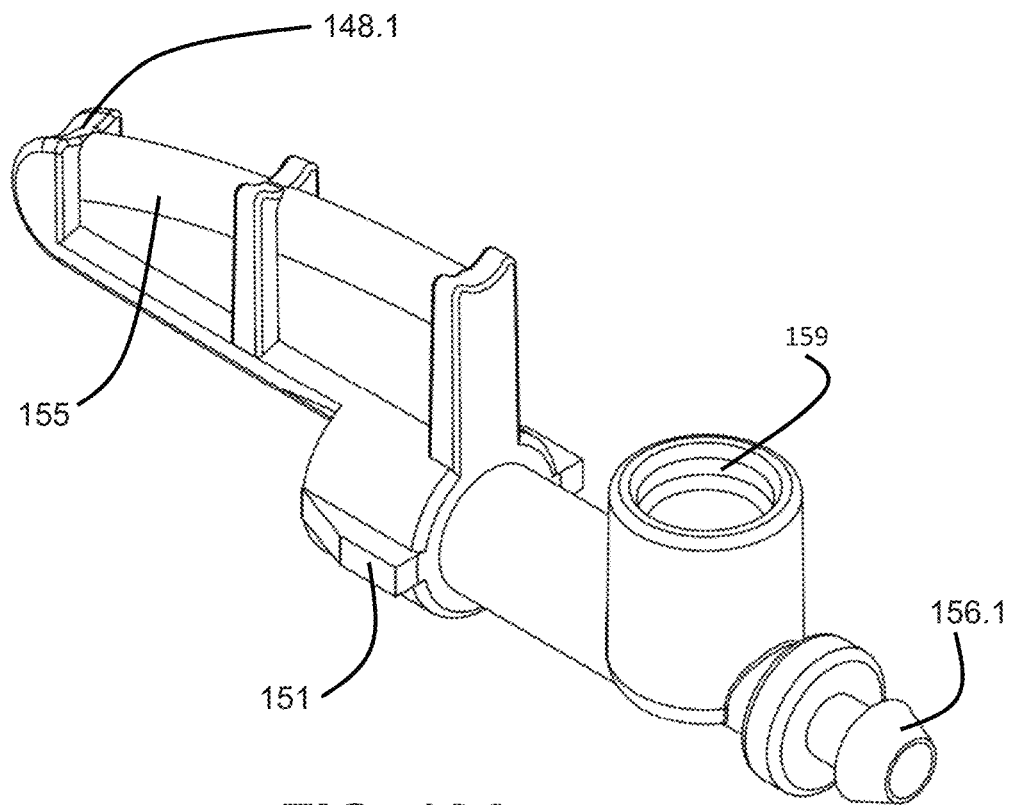
FIGS. 18A and 18B are top rear and top front perspective line drawings, respectively, of the collection adapter body of FIG. 10.
Figure 18B:
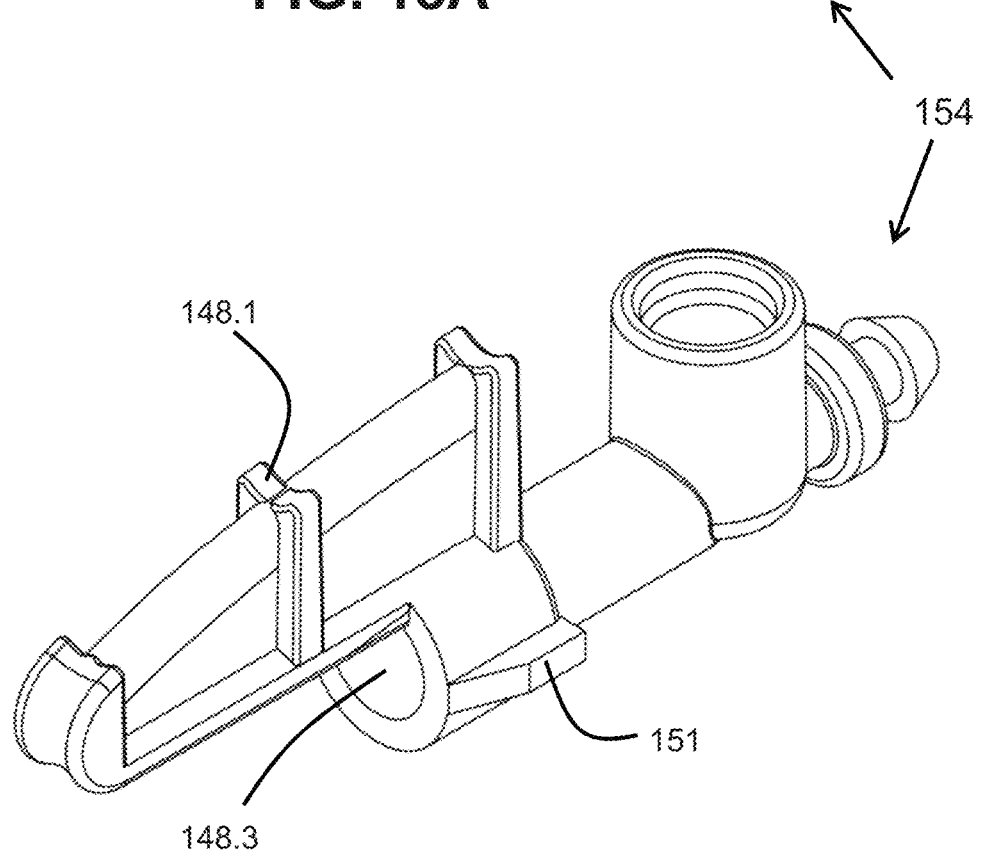
Figure 18C:
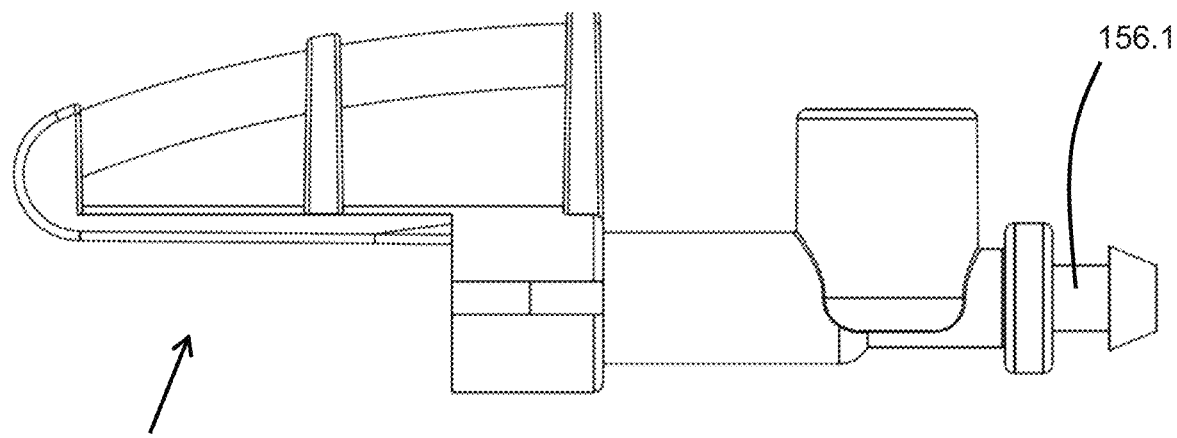
FIGS. 18C and 18D are side elevational and side cross sectional line drawings, respectively, of the apparatus of FIG. 18A, with FIG. 18D being a cross sectional representation of FIG. 18C as taken along the centerline of FIG. 18C.
Figure 18D:
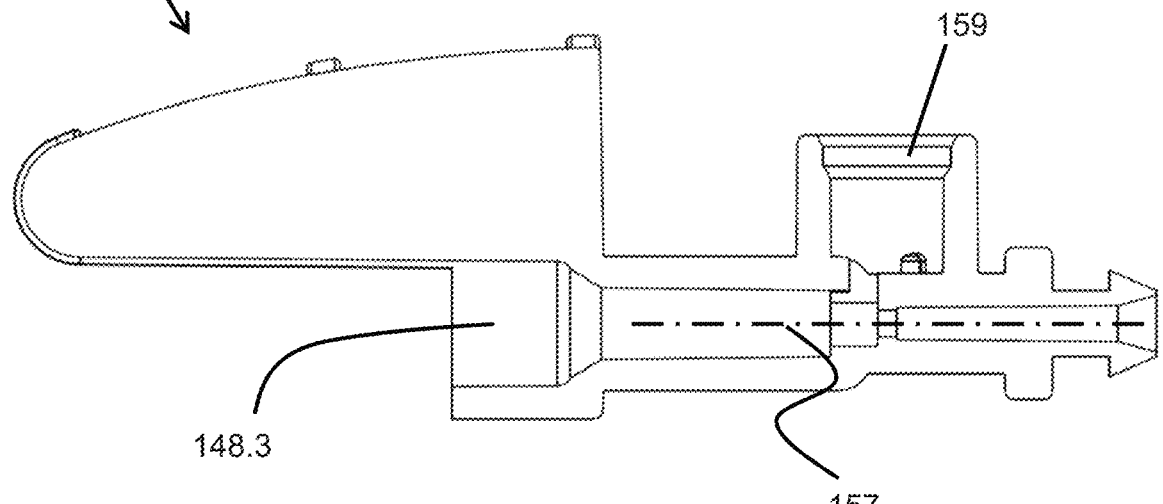

Holder top 124 receives within it a collection valve assembly 150, this assembly 150 being seen in side view on FIGS. 11B, 12B, 13B, and 14B. Holder top 124 includes a guide 124.1 that receives within it a correspondingly-shaped guided member 155 of body 154 (as seen in FIGS. 18A and 18B). This guiding chamber 124.1 extends generally above needle assembly 140 and leg 161.

In apparatus 120, holder top 124 provides for the internal placement of a needle assembly 140 and collection valve assembly 150 having cannula axes 147 and 157, respectively, that are generally parallel and vertically displaced from one another (as best in FIG. 11B). However, other embodiments of the present invention are not so limited. For example, yet other embodiments include a collection valve assembly having a cannula axis that is tilted relative to the cannula axis of the first needle, such that the collection cavity 121.2 is tilted upward, toward the face of the user during usage. Such embodiments further contemplate needle assemblies 140 that retract generally into the interior of main body 121.2, but not necessarily into the collection cavity. Still further, although FIGS. 11A and 11B show cannula axes 147 and 157 being parallel and displaced, yet other embodiments contemplate the axes being coincident. In such embodiments, it is contemplated that the first and second cannulas 142 and 152 can be unitary, such that both the needle assembly 140 and the cannula 152 retract from a first, ready-to-use position to a second, used position, after removal of catheter assembly 130 or actuation of some other retraction-causing feature.

Figure 16A:
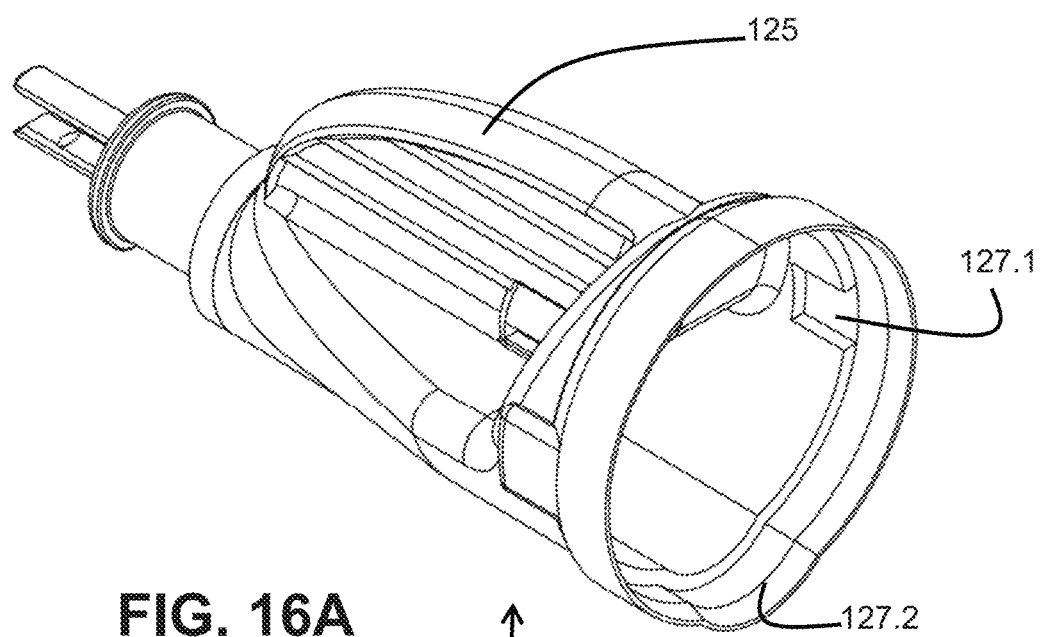
FIGS. 16A and 16B are top rear and top front perspective line drawings, respectively, of the holder top of FIG. 10.
Figure 16B:
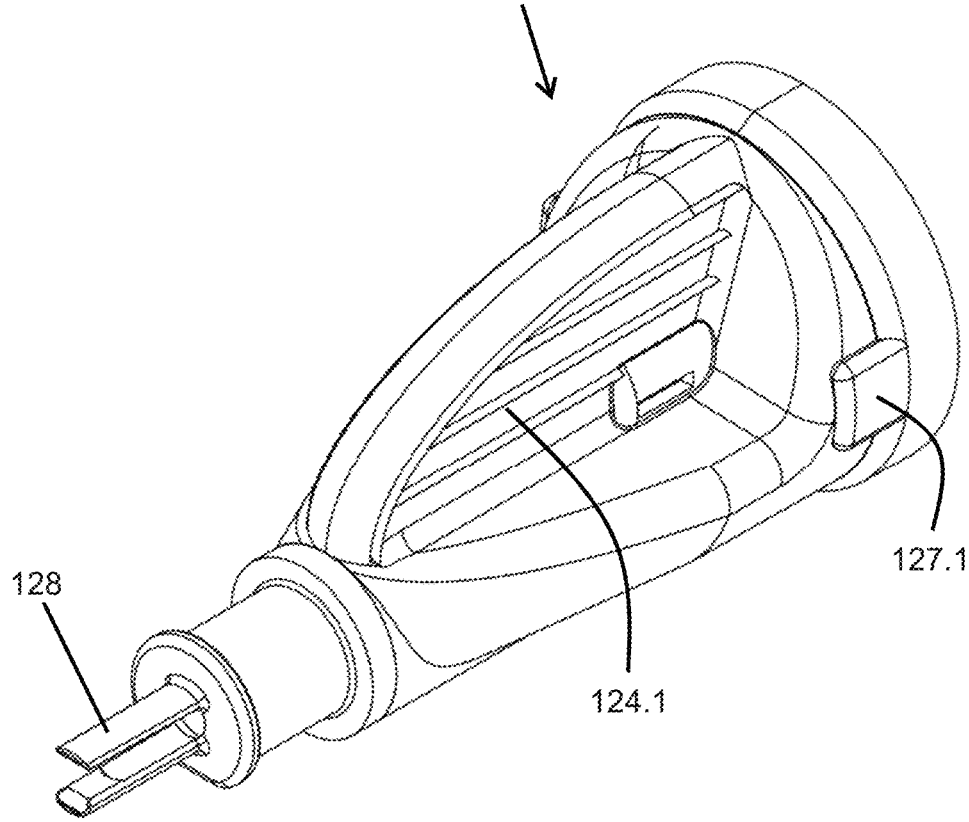
Figure 16C:
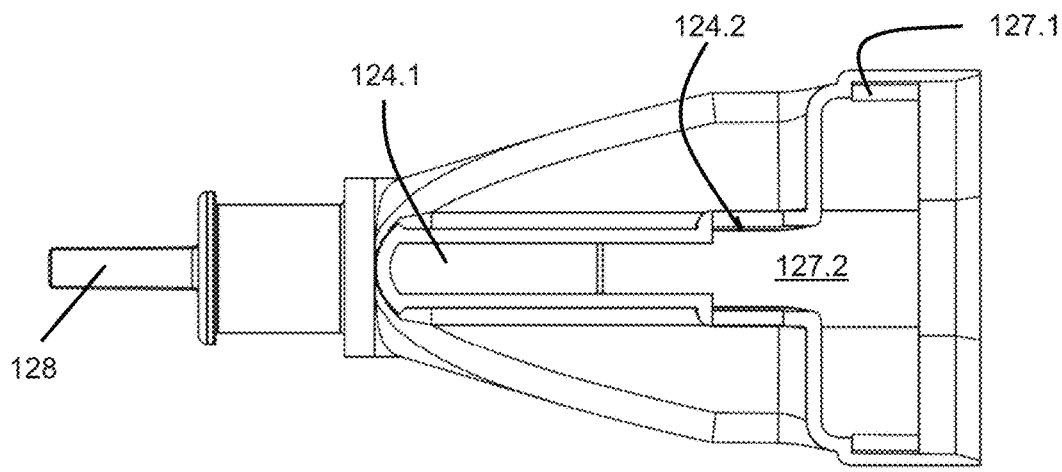
FIGS. 16C, 16D, and 16E are top plan, side elevational, and cross sectional line drawings, respectively, of the apparatus of FIG. 16A.
Figure 16D:
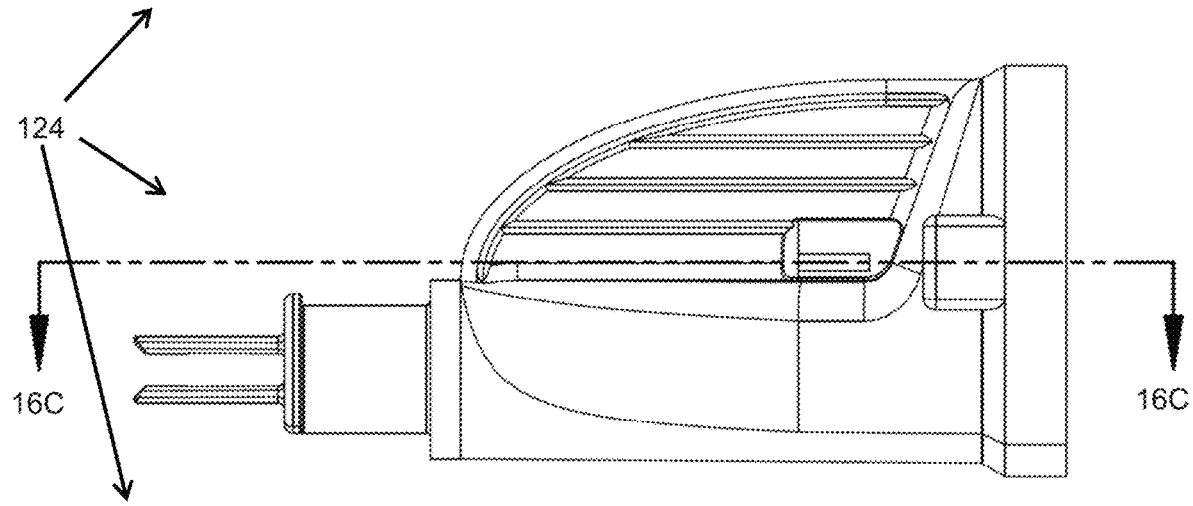
Figure 16E:
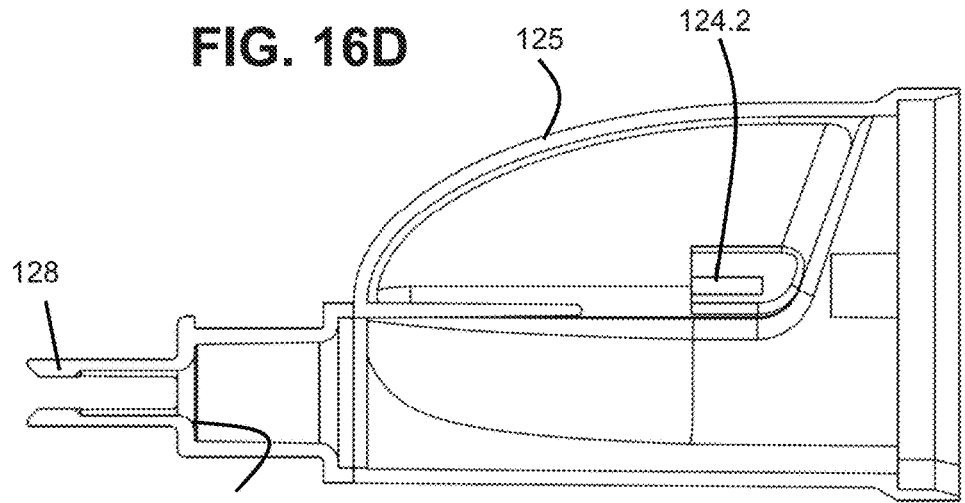

Referring to FIGS. 16C and 16E, it can be seen that holder top 124 includes a slot 124.2 that is adapted and configured to receive within it a corresponding guiding ear or locking tab 151 of adapter body 154 (as best seen in FIGS. 18A and 18B). The coaction of slot 124.2 and tab 151 provides for alignment of holder body 154 relative to holder top 124 (and therefore alignment with needle assembly 140). Referring to FIG. 18B, it can be seen that tab 151 in some embodiments provides a unidirectional, snap fit. Tab 151 has an angled, expanding leading edge to assist in temporary expansion of guide 124.1 during assembly, yet also includes a squared-off trailing edge that makes holder body 154 resistant to accidental disassembly and removal, the outermost diametral portions of ear 151 being in interference with portions of body 124 after the entire tab 151 is contained within slot 124.2, such that the temporarily expanded holder top 124.1 snaps back into place.

FIG. 11B shows a cross sectional view of a needle assembly 140. Needle assembly 140 preferably includes a beveled, sharp-tipped needle 142 that is fixed to the internal surfaces of a shuttling adapter 144. Cannula 142 is adapted and configured to extend within flexible lumen 132 of catheter 130. The tip of cannula 142 extends beyond the end of flexible lumen 132. During insertion of needle 142 and lumen 132 into the vein of a patient, needle 142 provides a stiffening function that maintains the cylindrical shape of lumen 132, preventing buckling of lumen 132 during insertion of the needle 142 and catheter 130 into the vein of the patient.

FIG. 17 show additional views of the adapter body 144 of needle assembly 140. Body 144 includes a front cylindrical cavity to which cannula 142 is attached, and which establishes a centerline 147 of cannula 142. Body 144 further includes a plurality of ridges 146.1 that assist in aligning and guiding an end of spring 146 (as can be seen in FIG. 11B). Body 144 further includes a shoulder 146.2 that receives an end 148.2 of spring 146, and against which spring 146 exerts a load.

The proximal end of body 144 is adapted and configured to receive within it an end of tube 148. FIG. 17C shows an internal cylindrical cavity 148.2 that receives the end of tube 148. As tube 148 exits from body 144, the tube makes a right angle turn through tube holding feature 148.4. It can be seen that feature 148.4 includes a generally semi-cylindrical shape that receives the outer diameter of the tube. However, this cylindrical shape is opened to the proximal end of body 144 by a V-shaped pair of upper and lower walls. As best seen in FIG. 17C, these angularly-shaped walls narrow down to a minimum distance that is large enough to permit tube 148 to be squeezed past these walls during assembly, but small enough to prevent the assembled and inserted, right-angled tube from escaping the semi-cylindrical aperture. The placement of tube holding feature 148.4 on a side of body 144 provides for less impedance by tube 148 on the retraction on needle assembly 140, by placing the sharpest turn radius of tube 148 held firmly within body 144. Therefore, very little of the spring force is consumed by any requirement to make a sharp bend in tube 148 as it retracts (referring to FIGS. 13A and 14A).

As best seen in FIG. 11B, needle assembly 140 is acted upon by a spring 146 that is located between the shoulder 146.2 of adapter 144 and a recess 146.3 of holder top 124 (as best seen in FIG. 16E). FIG. 4 shows needle assembly 140 inserted fully within catheter assembly 130, with the resultant maximum compression of spring 146. Preferably, spring 146 is a coil spring, although it is appreciated that various devices and methods can be used to bias apart adapter 144 and the forward shoulder of holder top 124. It can also be seen in FIG. 4 that cannula 142 extends through the distalmost end of valve 138, and thus provides fluid communication from the tip end aperture of needle 142, to the proximal-most opened end of adapter body 144. Tube 148 continues the path of fluid communication from adapter body 144 to adapter body 154, as will be discussed later.

Some embodiments of the present invention further include a sliding member 160 that can provide a plurality of functions with an apparatus 120. As one example, and as best seen in FIGS. 11A and 11B, sliding member 160 includes a cover 163 that includes an aperture 166 through which second needle 152 extends. Further, FIG. 11A shows that extending distally and on the bottom side of sliding member 160 is a leg 161 that fits generally underneath and guides the distal end of needle assembly 140. Still further, sliding member 160 includes a pair of outwardly extending ears 164 that coact with the main body to prevent sliding member 160 from moving distally forward from the first position 111, shown in FIGS. 11A and 11B. Sliding member 160 further defines a pocket 127.4 that provides placement of needle assembly 140 in both the partially retracted and fully retracted states (as seen in FIGS. 13B and 14B, respectively). Still further, the ears 164 of sliding disk 160 coact with main body 121.1 to prevent distal-direction movement of the cover 163 in the final, used configuration (as shown in FIGS. 14A and 14B).

Figure 19A:
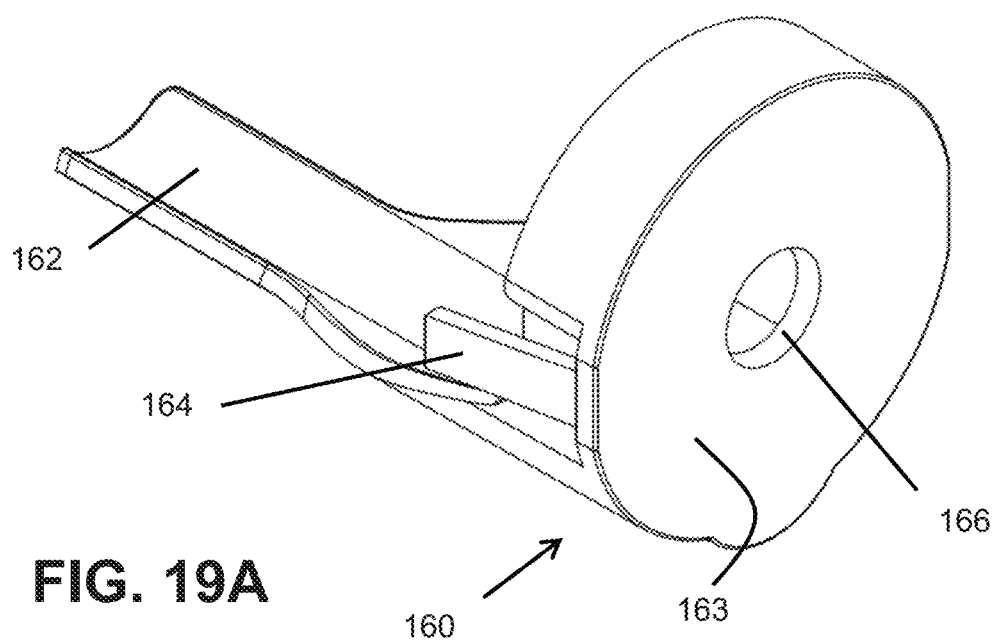
FIGS. 19A and 19B are top rear and top front perspective line drawings, respectively, of the sliding disc member of FIG. 10.
Figure 19B:
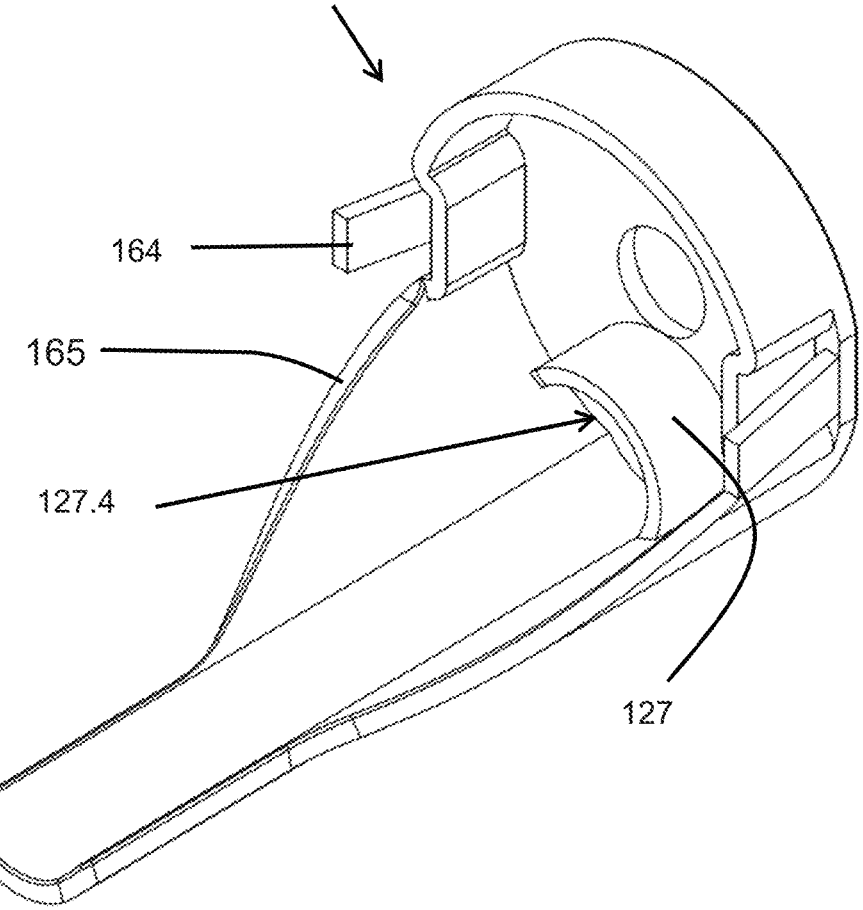
Figure 19D:
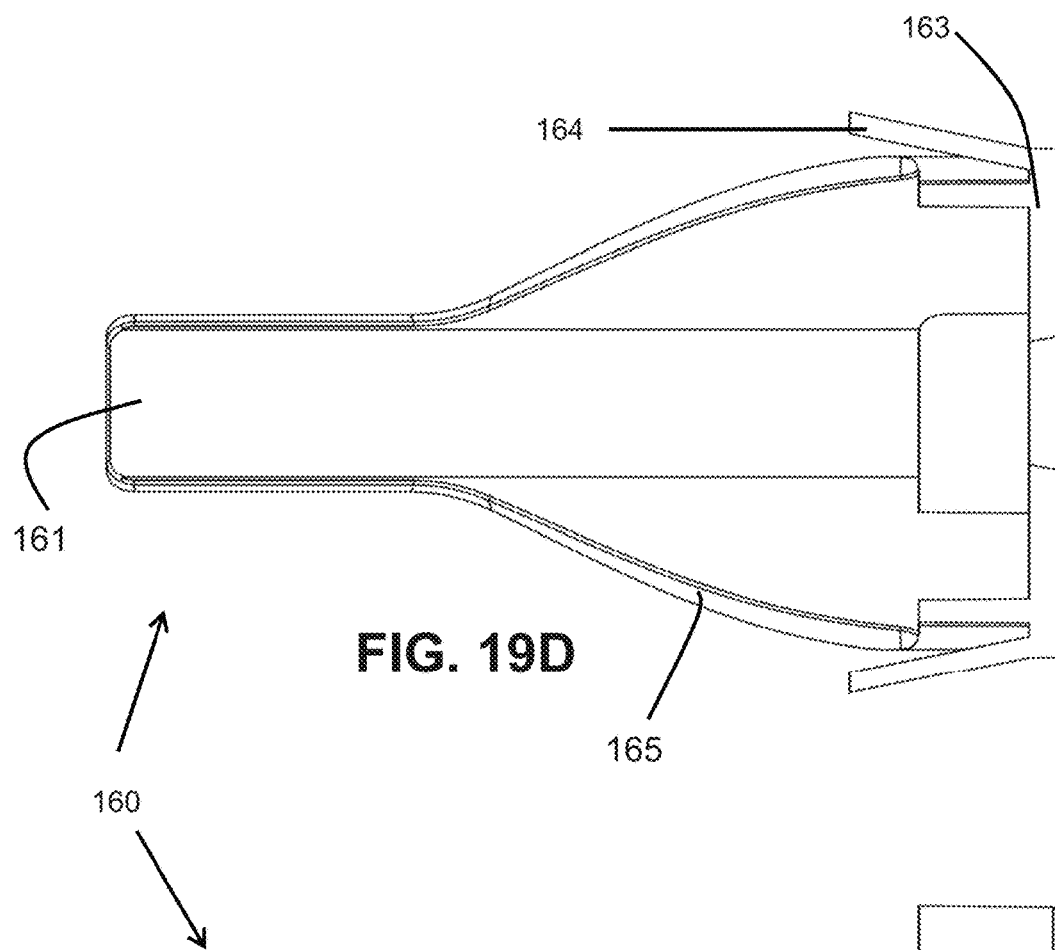
FIGS. 19C and 19D are side elevational and top plan views, respectively, of the apparatus of FIG. 19A, with FIG. 19D being the view looking down from line 19D-19D of FIG. 19C.
Figure 19C:
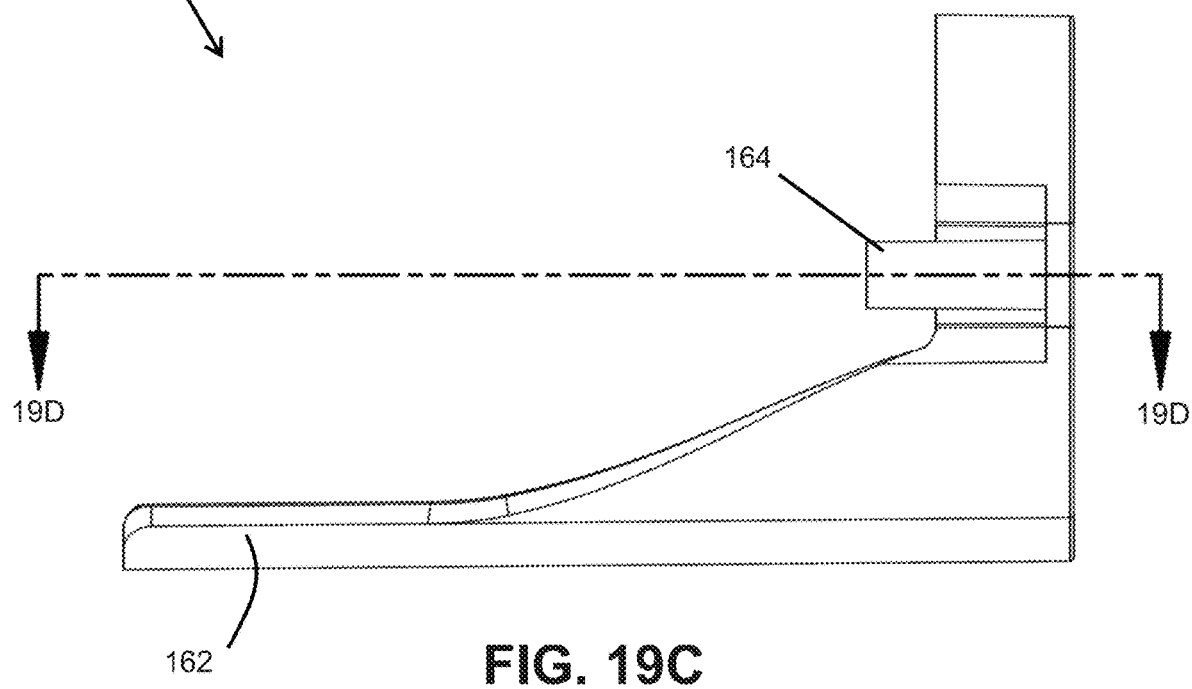
Figure 19E:
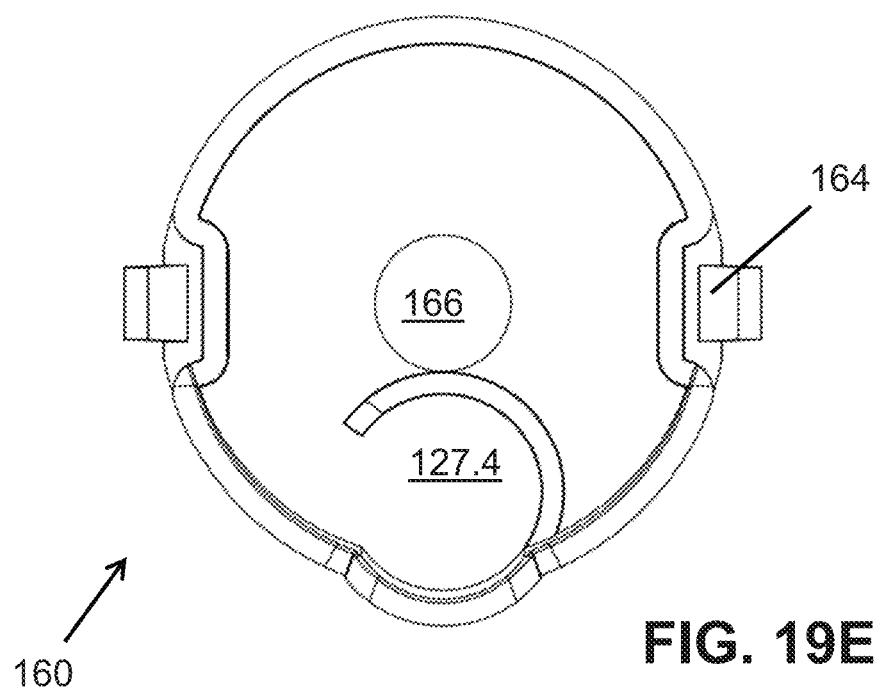
FIGS. 19E and 19F are front end and rear end views, respectively, of the apparatus of FIG. 19A.
Figure 19F:
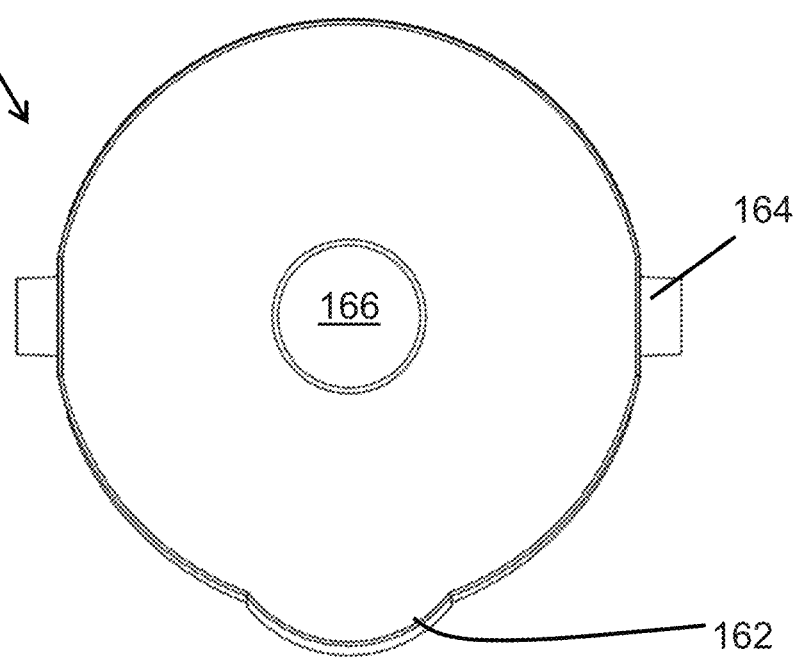

Referring to FIGS. 11B and 19D, a disk leg 161 operating as a guide for adapter 144 can be seen (leg 161 preferably not being engaged with adapter 144). A first latching mechanism between disk 160 and holder top 124 establishes the relative locations of needle assembly 140 and disk 160 in the first, ready to use position 111. A second latching mechanism establishes the relative positions of disk 160 and holder body 126, in the final, used second position 112. Disk 160 sits in a relaxed position between the holder top and holder body with a slight interference fit. In a manner that will be described later, leg 161 of disk 160 maintains radial alignment within the holder body 124 and acts as a guide to needle assembly 140 in a forwardmost position 111, with spring 146 under near-maximum compression, during a first mode of operation of apparatus 120.

Sliding member 160 is also shown in FIG. 19. Sliding member 160 includes a disk-shaped proximal end 163 that includes within it a generally centered aperture 166. A pair of flexibly hinged members or ears 164 extends generally outward on opposing sides of member 160. A leg 161 extends distally from the inner face of cover 163, and has a generally curved shape to it as seen in FIGS. 19E and 19F. Sliding member 160 further includes a semi-cylindrical wall 127 that defines therein a pocket 127.4.

Flexible ears 164 coact with complementary-shaped distal and proximal guide/stop grooves 127.1 and 127.3, respectively. These guide/stop grooves include a short length in the axial direction adapted and configured to receive the distal end of the ear, and provide guidance of the ear during sliding contact. The guide/stop grooves further include a distalmost endwall that is adapted and configured to coact with the corresponding ears to prevent distal motion beyond a first distalmost position (when the apparatus 120 is ready to be used) and a second distalmost position (after the device has been used, and the collection container withdrawn).

Distal guide/stop 127.1 can be seen in FIGS. 16A, 16B, and 16C. Proximal guide/stop 127.3 can be seen formed into holder body 126 in FIGS. 20B, 20C, and 20D. Ears 164 of sliding member 160 coact with proximal grooves 127.1 to limit the distalmost travel of member 160 in the first position (as can be seen in FIG. 12A). However, ears 164 are adapted and configured to not interfere with the sliding motion of member 160 from the first position toward the second position. In the fully extended and final position (as seen in FIG. 14A), ear 164 coacts with groove 127.3 to stop movement of member 160 in a distal direction after sliding member 160 is fully in the second position 112.

Figure 20A:
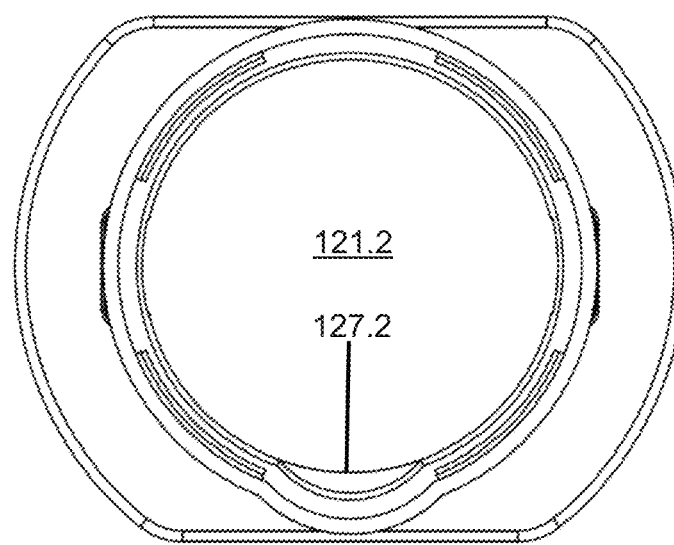
FIGS. 20A and 20B are rear elevational and top rear perspective line drawings, respectively, of the holder body of FIG. 10.
Figure 20B:
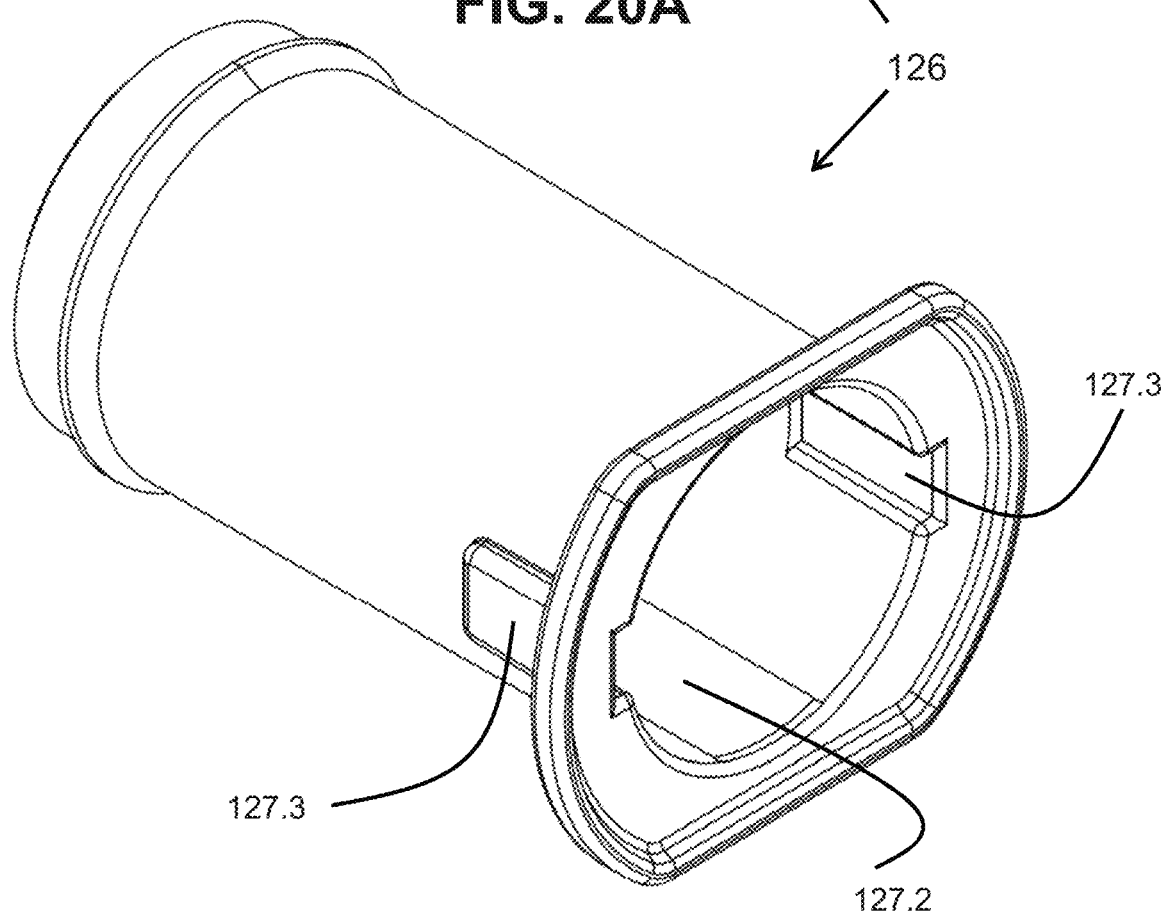
Figure 20C:
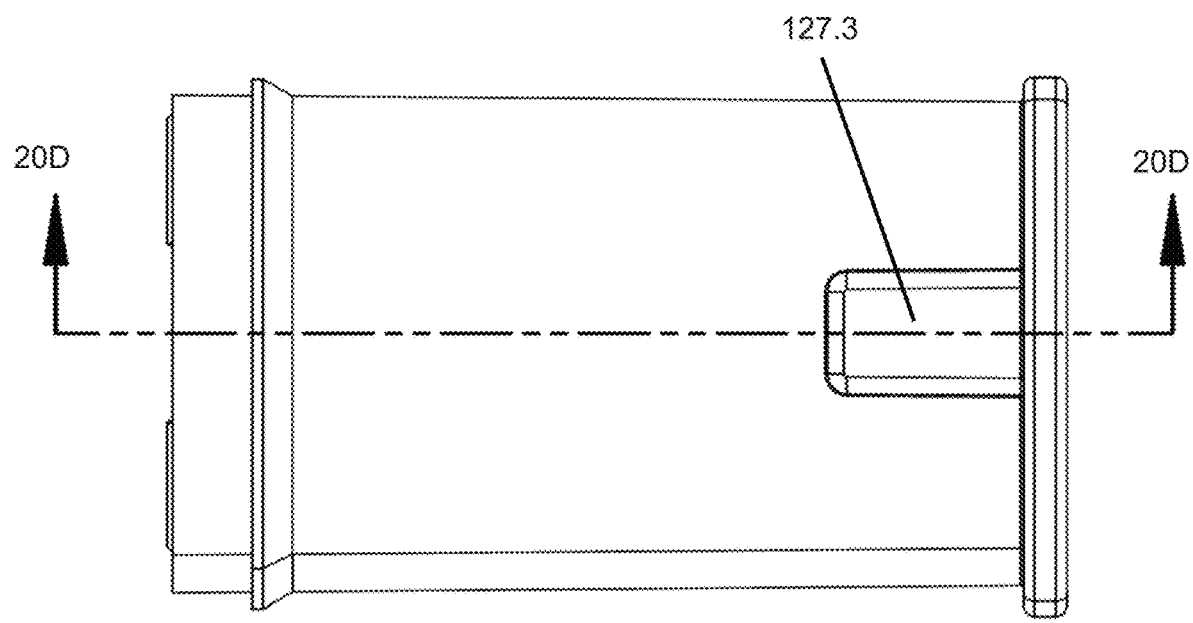
FIGS. 20C and 20D are side elevational and cross sectional line drawings, respectively, of the apparatus of FIG. 20A.
Figure 20D:
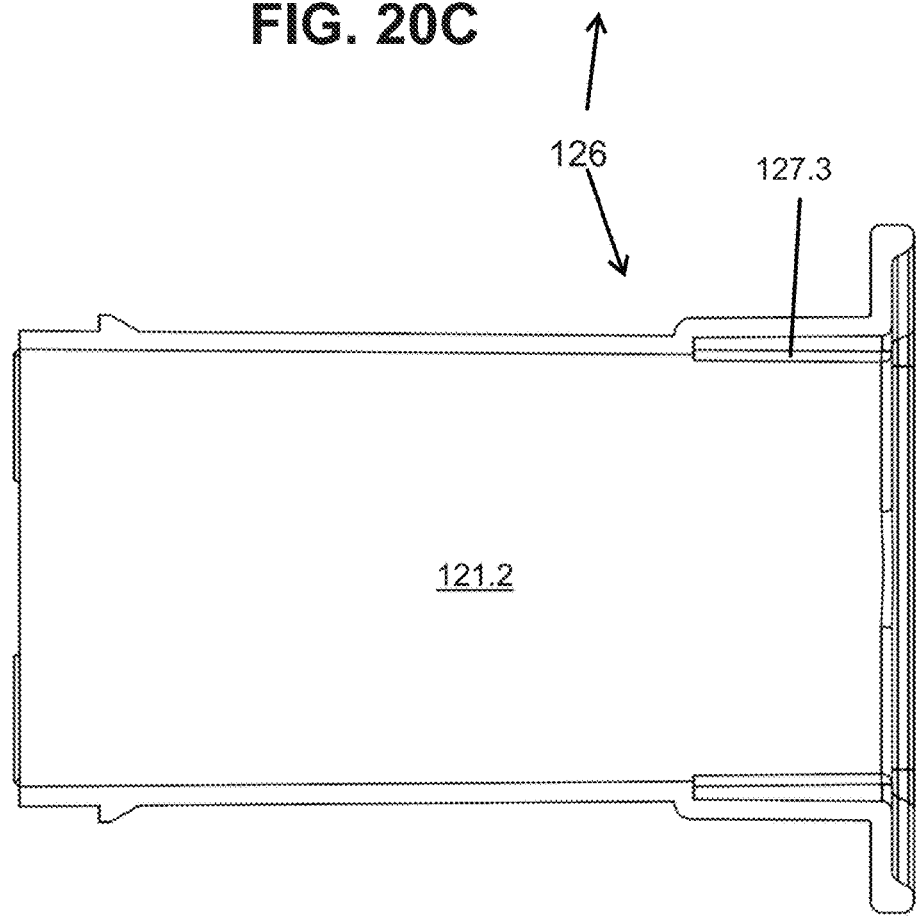
Figure 21A:
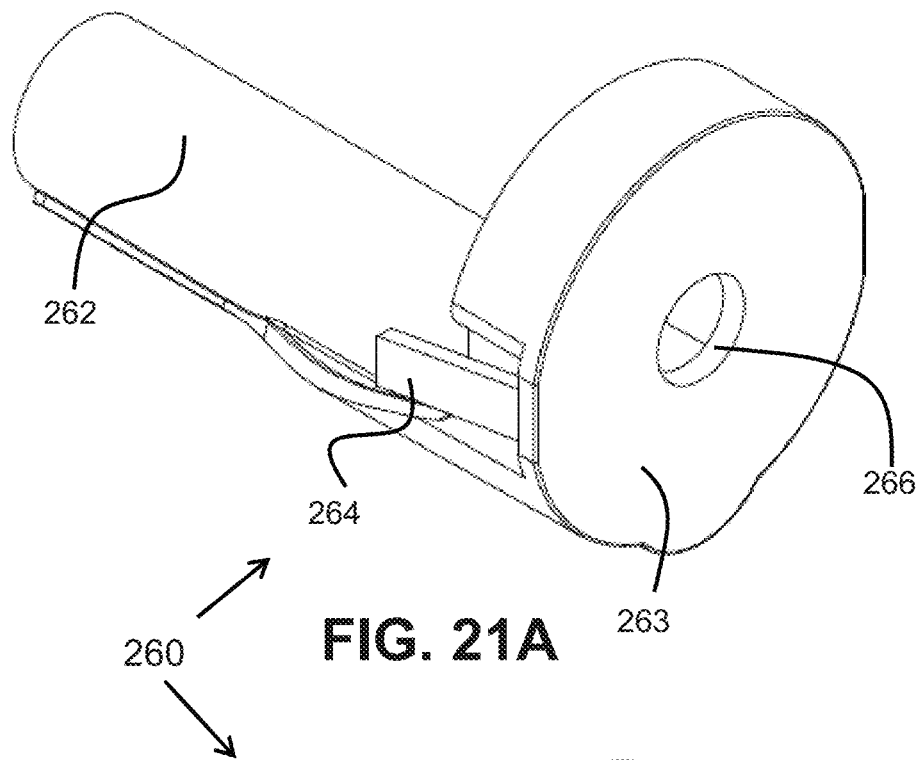
FIGS. 21A and 21B are top rear and top front perspective line drawings, respectively, of an alternative to the sliding disc member of FIG. 10.
Figure 21B:
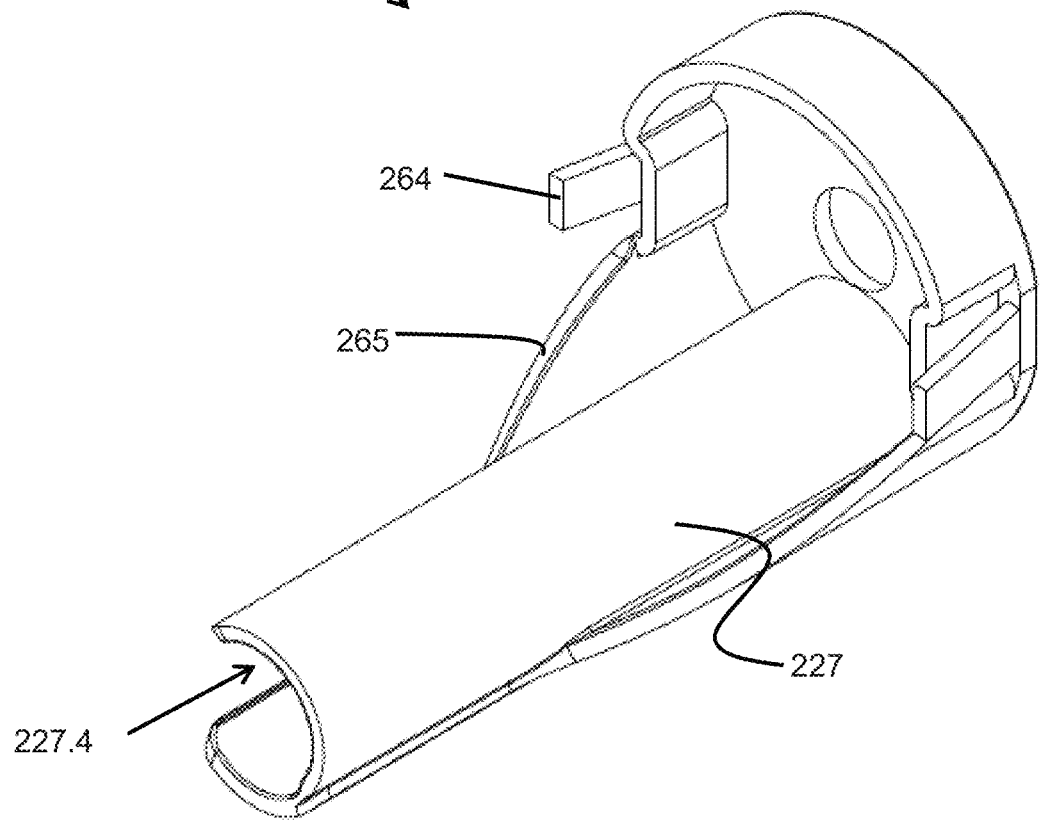
Figure 21C:
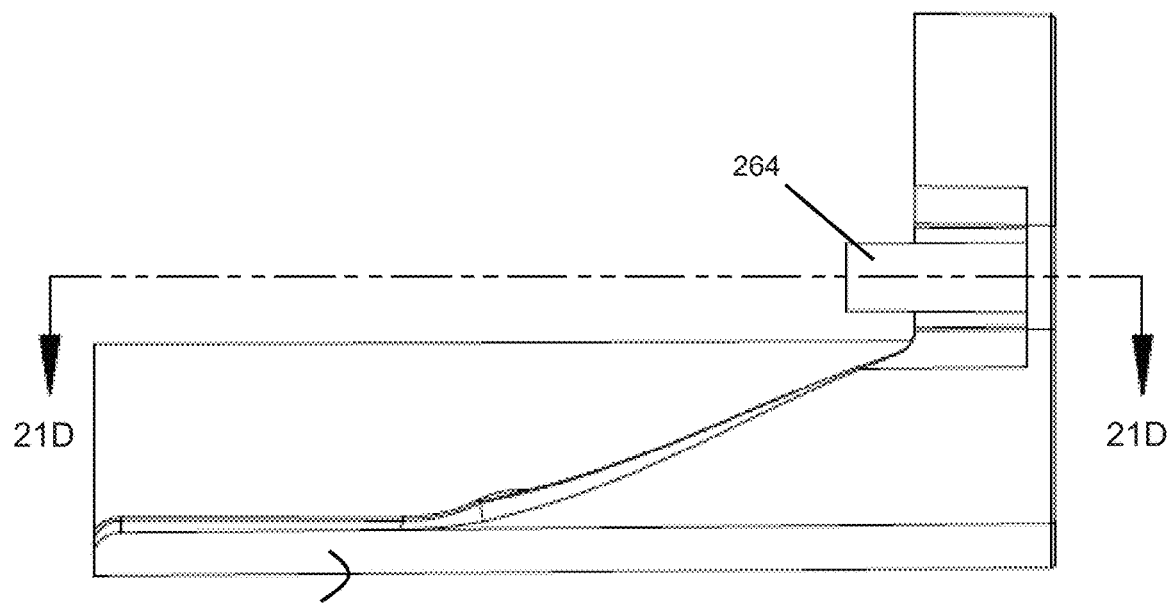
FIGS. 21C and 21D are side elevational and top plan views, respectively, of the apparatus of FIG. 21A, with FIG. 21D being the view looking down from line 21D-21D of FIG. 21C.
Figure 21D:
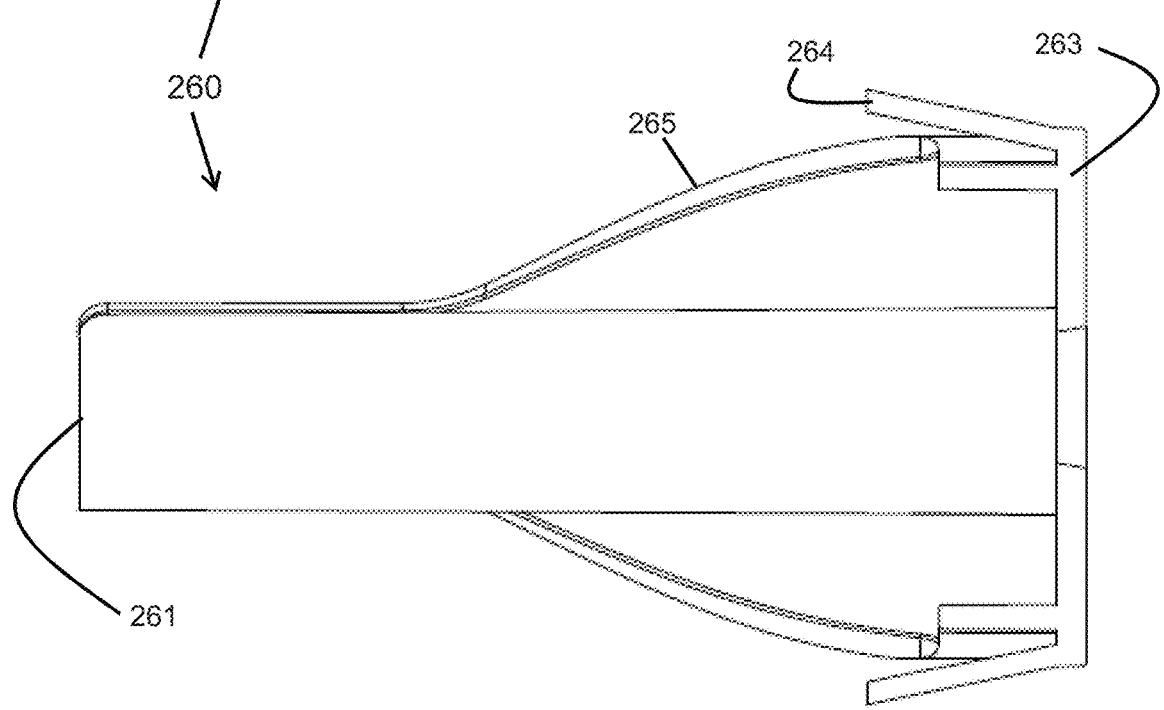
Figure 21E:
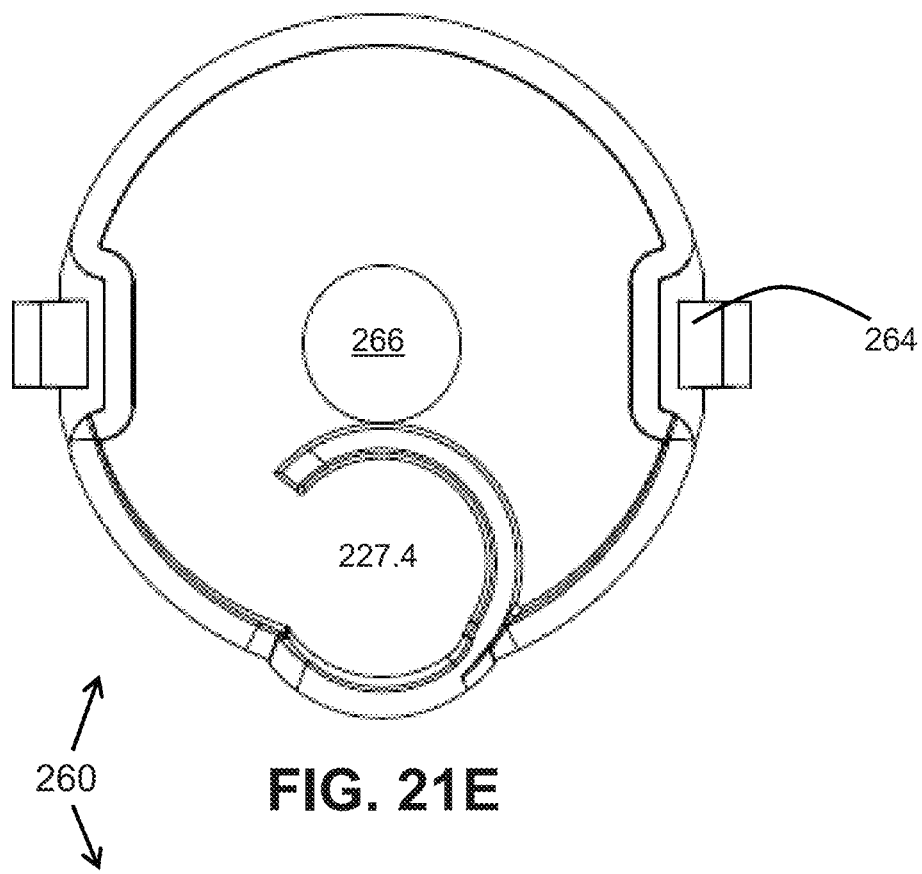
FIGS. 21E and 21F are front end and rear end views, respectively, of the apparatus of FIG. 21A.
Figure 21F:
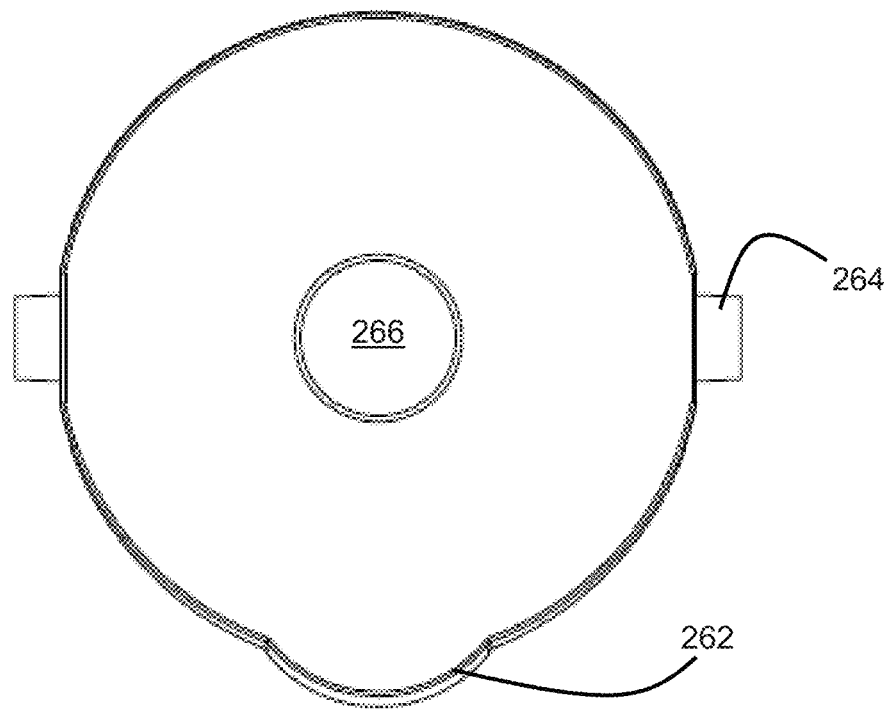

Sliding member 160 further includes a guiding feature 162 that has a shape complementary to a guiding feature 127.2, the latter being shown in FIG. 20B and FIG. 16A. Complementary-shaped features 162 and 127.2 coact to guide sliding member 160 within the main body 121.1 of apparatus 120 (as also seen in FIG. 14B). The guiding feature 162 in some embodiments fulfills a second function as a leg 161 that fits under and generally close to the bottom of adapter body 144 (as seen in FIGS. 11B and 12B). The curved shape of this leg further assists in guiding adapter body 144 into pocket 127.4, as needle assembly 144 retracts from the first position 111 into the second (and intermediate) position 112' (as seen in FIG. 13B). It is understood that in some embodiments the needle body-guiding function of leg 161 and the sliding member-guiding function (relative to main body 121.1) of guiding feature 162 can be accomplished simultaneously with the tongue-like structure shown in FIG. 19B. However, yet other embodiments contemplate configurations of the sliding member 160 in which these two guiding functions are performed separately on a sliding member, and still further contemplate those embodiments in which these functions are accomplished not on the sliding member but on other structure of the apparatus 120.

FIGS. 11 and 12 show views of a portion of apparatus 120. A latching disk 160 can be seen located within a generally cylindrical aperture 129 of holder body 126. Disk 160 is preferably a single, molded piece having a forwardly-extending leg. Various features of disk 160 are adapted and configured to provide a first latching between disk 160 and retractable need assembly 140, and a second latching between disk 160 and either holder top 124 or holder body 126.

Collection valve assembly 150 is attached to internal support ribs of holder top 124. Disk 160 includes a small, central aperture that loosely fits around an outer diameter of a shoulder of adapter 154. Thus, disk assembly 160 is free to move relative to adapter body 154, and body 154 is held fixed by holder top 124. A flexible tube 148 provides fluid communication from adapter 144 and cannula 142 to one end of adapter body 154.

Referring briefly to FIG. 11B, it can be seen that adapter 154 establishes a centerline 157 generally within the center of chamber 121 of holder body 126. Adapter body 144 and cannula 142 establish a second centerline 147 that is generally parallel to, and offset from, centerline 157. However, it is understood that yet other embodiments of the present invention contemplate relative arrangements of the centerlines of needle assembly 140 and collection valve assembly 150, including non-parallel arrangements (in which centerline 157 and aperture 129 of holder body 126 would be angled upward, away from the patient, referring to FIG. 2) and also those embodiments in which centerlines 147 and 157 are not offset (such as when the two axes are generally aligned).

It can be seen that adapter 154 supports a cannula 152 that extends rearward toward the proximal opening 129 of holder body 126. A conical barb at the proximal end of adapter body 154 further support a flexible sheath 156 that generally surrounds and seals cannula 152 to adapter body 154. Preferably, sheath 156 is fabricated from a flexible material, such as a silicone rubber, and can therefore easily be compressed and collapsed around cannula 152. The proximal-most end of cannula 152 preferable includes a beveled, sharp tip for puncturing a collection vessel, as will be described later.

Adapter body 154 supports a porous filter 158 that provides a purging function for the interior volume of cannula 142, adapter body 144, tube 148, and adapter body 154. The proximal end of disk 160 includes a protrusion 162 that is shown in FIG. 6 as being held against a forward ledge of holder body 126.

FIG. 18 show various views of an adapter body 154 according to one embodiment of the present invention. Body 154 includes a proximal end having a coupling feature 156.1 that is inserted into, and seals around, the open end of flexible sheath 156. Adjacent to coupling 156.1 is a cylindrical collar that closely fits within aperture 166 of sliding disk member 160. Adjacent to this centering collar is a receptacle 159 that receives within it filter 158. Referring to FIG. 18D, it can be seen that receptacle 159 includes an aperture in the bottom that provides fluid communication to the flowpath extending along centerline 157, this flowpath beginning at the tip of needle 142 and extending to the tip of needle 152, and further into the collection reservoir when the collection reservoir is in place. By way of this secondary flowpath to filter 158, any trapped air within the main flowpath can be released through the filer. Once the filer cavity fills with blood, the blood coacts with the filter media to block any outward flow from receptacle 159. FIG. 18D also shows that the flowpath upstream of receptacle 159 leads to a tube port 148.3 that receives an end of flexible tube 148. The other end of the flexible tube is received within the tube port 148.2 that can be seen in FIG. 17.

Referring to FIGS. 18 and 11B, it can be seen that tube 148 extends from port 148.3 and wraps around the distal-most nose of body 154, and is supported by one or more guiding tube guiding features 148.1. FIG. 11B shows the tube extending between the guiding features 148.1 and flash window 125. Preferably, the portion of tubing proximate to flash window 125 is transparent. The tube then extends aft (i.e., toward the right in FIG. 11B), around the body 154, and past the shoulder wings 165 of sliding disk member 160 (see FIGS. 19B and 19D), and extends finally in a distal direction toward tubing guide 148.4 and into tube port 148.2 of first needle body 144. With this forward-backward-forward again path of tube 148 in the first position, the lower portion of the tube is free to extend aft (i.e., in FIG. 14B to the right) in the second position 112, and thus not impede the retracting motion of needle assembly 140. As best seen in FIG. 14A, it can be seen that tube 148 in the second position extends generally toward one side of the centerline 147, with the end of tube 148 being received within tube holding feature 148.4 of adapter 144.

Apparatus 120 operates in several different modes. FIG. 10 is an exploded view of a storage mode of operation, in which catheter assembly 130 is located at the distal-most end of holder top 124, with full compression of spring 146. Further, in this storage mode, sheath 156 is unpunctured, and maintains the sterility of the internal flowpath of assembly 120.

FIGS. 11A and 11B represent apparatus 120 in a first mode of operation, and with sliding member 160 and needle assembly 140 in a first position 111. Cap 122 has been removed, exposing the sharp tip of cannula 142 and the exterior of flexible lumen 132. The medical practitioner has access to hold the exterior of luer body 134, as well as the ability to hold the exterior of holder top 124 and holder body 126. The medical practitioner places the sharp tip of cannula 140 relative to a vein of a patient, and inserts the cannula 142 and flexible lumen 132 within the vein of the patient.

In the first mode of operation, the medical practitioner can bring a standard collection vessel 110 (not shown) through aperture 129 and into the opened proximal chamber 121 of holder body 126. The proximal end of body 126 includes a generally cylindrical chamber 121. The interior dimensions of the proximal end of holder body 126 are slightly greater than the outer diameter of the collection vessel. Therefore, the collection vessel enters aperture 129, and the face of the collection vessel can be brought into contact with the proximal end of sheath 156.

Preferably, the end of the collection vessel 110 is soft enough such that the medical practitioner can push the collection vessel against sheath 156 and the sharp tip of cannula 152. By continuing to push the collection vessel toward adapter 154, the sharp tip of cannula 152 penetrates the end of collection vessel 110, and enters the interior of the collection vessel. However, the flexible sheath 156 does not enter the collection vessel, and instead is compressed in buckling along cannula 152 and toward adapter body 154.

Once the tip of cannula 152 extends within the empty volume of collection vessel 110, fluid communication is established from the interior of the collection vessel through cannula 152 and adapter body 154, through tube 148, and into the interior flow passage of needle assembly 140. Since needle assembly 140 is exposed to blood within the patient's vein, blood can begin to flow through needle assembly 140 and tube 148, through collection valve assembly 150, and into collection vessel 110.

In order to prevent any hydraulic lockup, the interior of collection vessel 110 can be established at a pressure less than the pressure of the blood within the vein, or a suitable fluid induction device can be used. Still further, any trapped air within needle assembly 140, tube 148, and valve assembly 150 can escape through porous filter 158. However, filter 158 is preferably of a type in which the porosity of the filter is maintained only so long as the filter does not contact blood (such as a Porex® material). Upon contact with the blood, the filter media loses porosity, such that there can be no further leakage of either trapped air or blood through the filter. As blood flows through tube 148, it can be seen by the medical practitioner through a transparent window 125 within holder top 124. The medical practitioner maintains collection vessel 10 within holder body 126 and in fluid communication with the vein of the patient until sufficient blood has been collected. Multiple collection vials maybe used.

After the medical professional has collected sufficient blood, the compression is relieved and the collection vessel 10 is withdrawn. The Adapter 144 assembly still remains in a distal position, and under spring load, until the Luer assembly 130 has separated from the holder top 124. The relationship between the luer body 134, Holder top Legs 128 and adapter 144 receiving flats 145 prevent movement.

Once the user advances the catheter luer assembly in a distal direction beyond legs 128, there is nothing to prevent leg 128 from flexing outward. This outward flexing releases Adapter 144 so it can move in a proximal direction, retracting toward the proximal end of holder body 126. Needle assembly 140 can move rearward toward a receiving pocket on the end of disk 160, as seen in FIGS. 12A and 12B. Luer assembly 130 has been removed from its frictional fit over the ears 128 of body 124, thus relieving the normal force applied between the flat 145 of body 144 and the tips of fingers 128. As shown in FIGS. 12A and 12B, with the release of the compression of the fingers into the grooves, needle assembly 140 begins to move from the first position 111 to the second position 112. As shown in FIG. 12B, first needle adapter body 144 is free to move and be guided by the curvature of leg 161. Both disk 160 and needle assembly 140 therefore move toward the proximal end of the body holder.

The beginnings of this movement can be first seen in FIGS. 13A and 13B. Under the influence of the expanding spring 146, needle body 144 has been urged into pocket 127.4 of sliding member 160 and into an intermediate second position 112'. As the proximal-most end of adapter body 144 abuts the internal face of pocket 127.4, the spring force is further exerted on sliding member 160 to move it toward the right. Adapter body 144 and sliding member 160 are shown in an intermediate second position 112', which is not a steady state location for the assembly as shown in FIG. 13B. In this position 112', there is still sufficient force being exerted by spring 146 to continue urging apart sliding member 160 and main body 121.1. The full seating of the needle assembly 140 in the receiving pocket 127.4 of disk 160 can be seen in FIG. 13B. Cannula 142 of needle assembly 140 retracts inward toward the interior of main body 121.1. The medical practitioner advances the catheter assembly 130 into the patient's vein, with the result that lumen 132 remains in fluid communication with the patient's vein. However, as needle assembly 140 retracts, the end of the needle assembly retracts past flexible valve 138, which acts as a one-way valve, and thereby closes and prevents any escape of the patient's blood from catheter 130.

FIGS. 14A and 14B show the remaining retraction of needle assembly 140 within holder body 126 to the final, at rest second position 112. As the assembly of the disk and needle retract, tube 148 begins to extend. FIGS. 13A and 13B show the intermediate retraction of needle assembly 140 relative to disk 160. FIGS. 14A and 14B show the completed and full retraction of the sliding disk 160 relative to holder 126. The aft face of disk 160 is biased by spring 146 to sit against a ledge or shoulder surrounding aperture 129 of holder body 126 and locks into place preventing any further movement. Tube 148 is shown in its position of maximum extension from the end of adapter 144 to the end of adapter 154. The sharp tip of cannula 142 is fully contained within holder top 124.

In some embodiments, the relationship between Adapter 144 and disk 160 is generally for guiding disk 160 to its full proximal position. Various embodiments do not include features that pre-stage activation upon insertion of a collection tube 110. The disk 60 statically stays positioned in the holder top 124 by a simple interference fit having a reverse draft. Multiple collection Tubes can be used without activation since activation) retraction of the needle assembly 140 and disk 160) does not occur until the Catheter Luer assembly 130 has separated from the Holder 124.

FIG. 21 show various views of an alternative sliding disk member 260 according to another embodiment of the present invention. Sliding member 260 is substantially the same as sliding member 160 previously described. However, member 260 includes a cylindrical receptacle 227 that extends generally along the length of leg 261. This cylindrically shaped receptacle is open on one side (as best seen in FIGS. 21B and 21E), through which an end of tube 148 can pass. Preferably, the axial length of receptacle 227 is greater than the length of body 144 of needle assembly 140. Further, receptacle 227 preferably extends distally a sufficient amount so that in the first position, the distal end wall of receptacle 227 extends past the proximal end of body 144. This substantially full length receptacle provides additional assurance of proper guiding of assembly 140 in its transition from the first position to the second position, as well as minimizing any possible buckling of spring 148 as it expands going from the first position to the second position.

Various aspects of different embodiments of the present invention are expressed in paragraphs X1, X2, X3, X4, X5, X6, X7, and X8 as follows:

X1. One aspect of the present invention pertains to an apparatus for collecting blood in a container and connecting to intravenous tubing, comprising a collection cavity adapted and configured to receive therein an end of a readily separable container; a first hollow needle having a first sharp tip, said first needle being adapted and configured for insertion of the first tip into a blood vessel; a second hollow needle having a second sharp tip extending into the collection cavity; and a catheter assembly having a body and a hollow lumen and receiving said first needle within the lumen, the first sharp tip extending from the distal end of the lumen, the catheter body having a proximal end adapted and configured for attachment to the intravenous tubing, said catheter body including a one-way valve; wherein said first needle and said main body are readily separable from said catheter assembly, and said one-way valve prevents flow of blood through the lumen when said first needle is separated from the lumen.

X2. Another aspect of the present invention pertains to an apparatus for collecting blood in a container and connecting to intravenous tubing, comprising a main body defining an interior adapted and configured with a readily separable container; a first retractable hollow needle having a first sharp tip, said first needle being movable from a first extended position in which the first sharp tip is exterior to said main body to a second retracted position in which the first sharp tip is within the interior; a second hollow needle having a second sharp tip, said second tip not extending outside of said main body; and a catheter assembly having a body and a hollow lumen and receiving said first needle within the lumen, the catheter body having a proximal end adapted and configured for attachment to the intravenous tubing; wherein said first needle and said main body are readily separable from said catheter assembly, said first needle automatically retracting to the second position in response to separating said first needle from said catheter assembly.

X3. Yet another aspect of the present invention pertains to a method for obtaining a sample of blood in a container from the circulatory system of a biological unit, comprising providing a hand-held device defining an interior including a collection cavity and including first and second hollow needles in fluid communication with each other and a catheter surrounding the first needle; inserting the first needle and the surrounding catheter into the circulatory system; inserting the second needle into the container; establishing fluid communication from the first needle to the container; separating the first needle and the catheter; and automatically retracting the first needle into the interior after said separating.

X4. Still another aspect of the present invention pertains to an apparatus for collecting blood in a container, comprising a main body including a collection cavity adapted and configured to receive therein an end of a separable container; a first retractable hollow needle slidable within said main body and having a first sharp tip, said first needle having a first extended position for insertion of the first tip into a blood vessel and a second retracted position in which the first tip is protected by said main body; a spring configured to urge said first needle into the second position; a second hollow needle attached to said main body and having a second sharp tip extending into the collection cavity; and a catheter having a hollow lumen and receiving said first needle within the lumen when said first needle is in the first position.

X5. Still another aspect of the present invention pertain to an apparatus for collecting blood in a container, comprising a main body including a collection cavity adapted and configured to receive therein an end of a separable container; a sliding member guided to slide along a path within the collection cavity from a first position to a second position and including a cover defining an aperture; a first retractable hollow needle coupled to said main body and having a first sharp tip, wherein in the second position the first tip is protected within said main body; a second hollow needle attached to said main body and having a second sharp tip extending through the aperture in the first position into the collection cavity; and a catheter having a hollow lumen and receiving said first needle within the lumen when said first needle is in the first position; wherein said first needle is separated from said lumen in the second position, and said cover protects the user from accidental contact with said second needle in the second position.

X6. Yet another aspect of the present invention pertains to an apparatus for collecting blood in a container, comprising a main body including a collection cavity adapted and configured to receive therein an end of a separable container; a first retractable hollow needle slidable within said main body and having a first sharp tip, said first needle having a first extended position for insertion of the first tip into a blood vessel and a second retracted position in which the first tip is protected within said main body; a second hollow needle fixedly attached to said main body and having a second sharp tip extending toward the collection cavity; and a catheter having a hollow lumen and receiving said first needle within the lumen when said first needle is in the first position; wherein said first needle is distal to said second needle in the first position, said first needle is separated from said lumen in the second position, and which further comprises a first needle body attached to said first needle, wherein in the second position said first needle body is received within the collection cavity.

X7. Still another aspect of the present invention pertains to an apparatus for collecting blood in a container, comprising a main body including a collection cavity adapted and configured to receive therein an end of a separable container; a first retractable hollow needle slidable within said main body and having a first sharp tip, said first needle having a first extended position for insertion of the first tip into a blood vessel and a second retracted position in which the first tip is protected within said main body, said first needle being oriented along a first axis; a second hollow needle separate from said first needle and attached to said main body and having a second sharp tip extending into the collection cavity, said second needle being oriented along a second axis that is non-coincident with the first axis; and a catheter having a hollow lumen and receiving said first needle within the lumen when said first needle is in the first position; wherein said first needle is separated from said lumen in the second position.

X8. Yet another aspect of the present invention pertains to an apparatus for collecting blood in a container, comprising a main body including a collection cavity adapted and configured to receive therein an end of a separable container; a first retractable hollow needle slidable within said main body and having a first sharp tip, said first needle having a first extended position for insertion of the first tip into a blood vessel and a second retracted position in which the first tip is protected within said main body; a second hollow needle separate from said first needle and having a second sharp tip extending into the collection cavity a flexible tube providing fluid communication from said first needle to said second needle in the first position; and a catheter having a hollow lumen and receiving said first needle within the lumen when said first needle is in the first position; wherein said first needle is separated from said lumen in the second position.

Yet other embodiments pertain to any of the previous statements X1, X2, X3, X4, X5, X6, X7, or X8 which are combined with one or more of the following other aspects. It is also understood that any of the aforementioned X paragraphs include listings of individual features that can be combined with individual features of other X paragraphs.

Which further comprises a transparent member permitting visualization of the flow of blood to said second needle.

Which further comprises a second body coupled to said second needle and providing fluid communication from said first needle to said second needle, said second body including a gas purging valve that permits the escape of gas contained in the fluid flowpath from said first needle to said second needle.

Wherein said catheter body is coupled to said main body by a frictional fit.

Wherein said first needle and said second needle are unitary.

Wherein said first needle and said second needle are non-unitary.

Which further comprises means for automatically retracting said first needle.

Wherein said retraction means includes a spring.

Which further comprises means for preventing automatic retraction of the first needle.

Wherein said preventing means includes a plurality of fingers each received within a corresponding groove, said main body including one of said fingers or said grooves and first needle body including the other of said fingers or said grooves.

Wherein said preventing means includes a frictional fit between said catheter body and said main body.

Wherein after said separating and during said retracting the catheter remains inserted into the circulatory system.

Which further comprises blocking said retracting by said placing.

Wherein said providing includes a cover of the collection cavity, and which further comprises automatically locking the cover to prevent access by the user to the second hollow needle.

Wherein said locking occurs automatically by said separating and by removing the container from the collection cavity.

Which further comprises removing the container from the cavity after said collecting.

Which further comprises collecting blood within the container after said establishing and before said separating.

Wherein said establishing is by puncturing the container with the second needle.

Wherein the device includes a pocket and said retracting is into the pocket.

Wherein said retracting is into the collection cavity.

Wherein said first needle is supported by a needle body having a ridge, said main body includes a recess, and said spring urges the ridge apart from the recess.

Which further comprises a cover for the collection cavity, and said spring is configured to urge said cover to a position preventing access to said second hollow needle.

Wherein said spring is a coil spring.

Wherein said second needle has an axis, the collection cavity has a first length along the axis, said second needle extends into the cavity by a second length along the axis, and the second length is less than the first length.

Which further comprises a flexible sheath surrounding the second sharp tip.

Wherein said sliding member includes a flexible outwardly extending ear, said main body includes a groove adapted and configured to receive the ear therein, said ear and said groove coacting to prevent movement of said sliding member relative to said main body when said first needle is in the first position.

Wherein said sliding member includes a flexible outwardly extending ear, said main body includes a groove adapted and configured to receive the ear therein, said ear and said groove coacting to prevent movement of said sliding member relative to said main body when said first needle is in the second position.

Wherein said sliding member includes an internal pocket, said first needle is received within a first needle body, and said first needle body is coupled to said main body in said first position, and said first needle body is received within the pocket in the second position.

Wherein said sliding member includes a first feature having a cross sectional shape, said main body includes a second feature having a shape complementary to the shape of the first feature, and said first feature and said second feature coact to guide the sliding of said sliding member along the path.

Wherein the cavity has an inner diameter and the cover has an outer diameter substantially the same but less than the inner diameter.

Which further comprises a cover slidable within the collection cavity, said main body has a distalmost end, and said first needle is located between the distalmost end and the cover in the second position Which further comprises a cover slidable within the collection cavity from a first position in which an aperture of said cover surrounds said first needle, to a second position in which said cover closes the collection cavity and prevents access to said second sharp tip.

Which further comprises a spring adapted and configured to urge apart said main body and said first needle body.

Wherein said first needle body applies a force from said spring to urge said cover to the second position.

Wherein the first axis and the second axis are parallel.

Wherein the first axis and the second axis are displaced from one another.

Wherein the first axis and the second axis are not parallel.

Wherein the second axis extends upward relative to the first axis.

Wherein said tube is adapted and configured to provide fluid communication from said first needle to said second needle in the second position.

Wherein said main body includes a window, and said flexible tube can be viewed through the window.

Wherein in the first position said first needle is generally distal to said second needle, and in the second position said first needle is generally adjacent to said second needle.

Wherein said first needle is received within a first needle body, wherein said sliding member includes a receptacle for receiving said hollow needle body, said receptacle at least partially enclosing said hollow needle body in the first position.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. An apparatus for collecting blood in a separable container, comprising:
    a main body defining an interior and including a collection cavity adapted and configured to receive therein an end of a separable container;
    a sliding member guided to slide along a path within the collection cavity from a first position to a second position and including a cover defining an aperture;
    a first retractable hollow needle coupled to said main body and having a first sharp tip, wherein in the first position the first sharp tip is extended for insertion into a blood vessel and in the second position the first sharp tip is protected within said main body;
    a second hollow needle attached to said main body and having a second sharp tip extending through the aperture in the first position into the collection cavity; and
    a catheter having a hollow lumen and receiving said first retractable hollow needle within the hollow lumen when said first retractable hollow needle is in the first position; and
    a gas purging valve supported by said main body that permits the escape of gas contained in a fluid flowpath from said first retractable hollow needle to said second hollow needle;

wherein said first retractable hollow needle is separated from said hollow lumen in the second position, and said cover shields the second sharp tip of said second hollow needle within the collection cavity in the second position, wherein the fluid flowpath from said first retractable hollow needle to said second hollow needle is a first fluid flowpath, and said gas purging valve releases escaped gas into the interior through a second fluid flowpath.

2. The apparatus of claim 1, wherein said sliding member includes a flexible outwardly extending ear, said main body includes a groove adapted and configured to receive the ear therein, said ear and said groove coacting to prevent movement of said sliding member relative to said main body when said first retractable hollow needle is in the first position.

3. The apparatus of claim 1, wherein said sliding member includes a flexible outwardly extending ear, said main body includes a groove adapted and configured to receive the ear therein, said ear and said groove coacting to prevent movement of said sliding member relative to said main body when said first retractable hollow needle is in the second position.

4. The apparatus of claim 1, wherein said sliding member includes an internal pocket, said first retractable hollow needle is received within a first needle body, and said first needle body is coupled to said main body in said first position, and said first needle body is received within the internal pocket in the second position.

5. The apparatus of claim 1, wherein said sliding member includes a first feature having a cross sectional shape, said main body includes a second feature having a shape complementary to the shape of the first feature, and said first feature and said second feature coact to guide the sliding of said sliding member along the path.

6. The apparatus of claim 1, wherein the collection cavity has an inner diameter and the cover has an outer diameter substantially the same as the inner diameter but less than the inner diameter.

7. The apparatus of claim 1, wherein said first retractable hollow needle automatically retracts to the second position in response to separating said first retractable hollow needle from said catheter, and which further comprises means for automatically retracting said first retractable hollow needle.

8. The apparatus of claim 7, wherein said means for automatically retracting includes a spring in a state of compression in the first position.

9. The apparatus of claim 1, wherein said first retractable hollow needle automatically retracts to the second position in response to separating said first retractable hollow needle from said catheter, and which further comprises means for preventing automatic retraction of the first retractable hollow needle.

10. The apparatus of claim 9, further comprising a first needle body supporting said first retractable hollow needle, and wherein said means for preventing automatic retraction includes a plurality of fingers each received within a corresponding flattened area, said main body including one of said fingers or said flattened areas and said first needle body including the other of said fingers or said flattened areas.

11. The apparatus of claim 9, wherein said preventing means includes a frictional fit between said catheter and said main body.

12. The apparatus of claim 1, which further comprises a flexible tube providing fluid communication between said first retractable hollow needle and said second hollow needle, wherein said main body includes a window, and said flexible tube can be viewed through the window.

13. The apparatus of claim 1, wherein said catheter includes a luer adapted and configured for attachment to intravenous tubing.

14. The apparatus of claim 1, wherein said first retractable hollow needle and said second hollow needle are in a fluid flowpath adapted and configured to provide blood to the separable container.

15. The apparatus of claim 1, wherein said first retractable hollow needle is separate from said second hollow needle.

16. The apparatus of claim 1, which further comprises a flexible tube providing fluid communication between said first retractable hollow needle and said second hollow needle in both the first position and the second position.

17. The apparatus of claim 1, which further comprises a flexible sheath surrounding the second sharp tip.

18. The apparatus of claim 1, wherein said gas purging valve is adapted and configured to block the second fluid flowpath after contact with blood.

19. The apparatus of claim 1, which further comprises a spring adapted and configured to bias said cover to the second position, and after separation of said first retractable hollow needle from said hollow lumen said spring automatically urges said cover to shield said second hollow needle within the collection cavity.

20. The apparatus of claim 19, wherein after separation of said first retractable hollow needle from said hollow lumen said cover shields said first retractable hollow needle within the collection cavity.

\* \* \* \* \*